United States Patent
Post et al.

(10) Patent No.: US 11,447,715 B2
(45) Date of Patent: Sep. 20, 2022

(54) ODORANTS AND COMPOSITIONS COMPRISING ODORANTS

(71) Applicant: S H KELKAR & COMPANY LIMITED, Maharashtra (IN)

(72) Inventors: Freddy Post, Arnhem (NL); Leszek Doszczak, NL (NL); Nitesh Chaudhari, Maharashatra (IN)

(73) Assignee: S H KELKAR & COMPANY LIMITED

( * ) Notice: Subject to any disclaimer, the term of this patent is extended or adjusted under 35 U.S.C. 154(b) by 259 days.

(21) Appl. No.: 16/755,872

(22) PCT Filed: Oct. 16, 2018

(86) PCT No.: PCT/EP2018/078302
§ 371 (c)(1),
(2) Date: Apr. 13, 2020

(87) PCT Pub. No.: WO2019/076933
PCT Pub. Date: Apr. 25, 2019

(65) Prior Publication Data
US 2021/0207059 A1    Jul. 8, 2021

(30) Foreign Application Priority Data

Oct. 17, 2017  (IN) .............................. 201721036891
Dec. 13, 2017  (EP) ..................................... 17206935

(51) Int. Cl.
| | |
|---|---|
| *C07C 45/45* | (2006.01) |
| *C11B 9/00* | (2006.01) |
| *A23L 27/00* | (2016.01) |
| *A61L 9/00* | (2006.01) |
| *A23L 27/20* | (2016.01) |
| *A61L 9/015* | (2006.01) |
| *C07C 249/08* | (2006.01) |
| *C07C 251/40* | (2006.01) |
| *A61L 9/01* | (2006.01) |

(52) U.S. Cl.
CPC .......... *C11B 9/0007* (2013.01); *A23L 27/203* (2016.08); *A23L 27/204* (2016.08); *A23L 27/2024* (2016.08); *A23L 27/2026* (2016.08); *A61L 9/01* (2013.01); *A61L 9/015* (2013.01); *C07C 45/45* (2013.01); *C07C 249/08* (2013.01); *C07C 251/40* (2013.01); *C11B 9/0015* (2013.01); *C11B 9/0061* (2013.01); *A23V 2002/00* (2013.01); *C07C 2601/02* (2017.05); *C07C 2601/04* (2017.05); *C07C 2601/08* (2017.05); *C07C 2601/14* (2017.05); *C07C 2601/16* (2017.05)

(58) Field of Classification Search
CPC .... C11B 9/0015; C11B 9/061; A23L 27/2024; A61L 9/01; C07C 45/45
See application file for complete search history.

(56) References Cited

U.S. PATENT DOCUMENTS

| | | |
|---|---|---|
| 4,448,713 A | 5/1984 | Boden |
| 4,613,706 A | 9/1986 | Sprecker et al. |

FOREIGN PATENT DOCUMENTS

WO    2005/110961 A1    11/2005

OTHER PUBLICATIONS

International Search Report and Written Opinion of PCT/EP2018/078302, dated Jan. 10, 2019.
Nasarow, "Synthese von tertiaren Alkoholen der allgemeinen Formeln R3C.C(OH) (CH3).CHR2 and R3C.C(OH) (CH3).CR3. Einwirkung von Methyl-magnesiumbromid auf verzweigte ketone", Berichte Der Deutschen Chemischen Gesellschaft, vol. 70, No. 4, Apr. 7, 1937, pp. 599-605.
Claude Lion; Jacques-Emile Dubois: "N° 484. Synthese de cotones beta,gamma-ethyleniques. Action des organomagnesiens allyliques sur les dimethyl-4,4 oxazolines-2 substituees", Bulletin De La Societe Chimique De France, No. 9-10, 1973, pp. 2673-2676, XP009509984.
Behrouz Fathi, Edgardo Giovannini: "Ober Umlagerungen bei der Cyclialkylierung von Arylpentanolen zu 2,3-Dihydro-1H-inden-Derivaten. 4. Mitteilung: Die saurekatalysierte Cyclialkylierung von 2,4-Dimethyl-2-phenyl[3-13C]pentan-3-ol", Helvetica Chimica Acta, vol. 85, Aug. 2, 2002, pp. 2083-2088.
Herbert C. Brown, James A. Sikorski, Surendra U. Kulkarni, Hsiupu D. Lee: "Hydroboration. 59. Thexylchloroborane-methyl sulfide. A new stable monohydroborating agent with exceptional regioselectivity", Journal of Organic Chemistry, vol. 47, No. 5, Feb. 1, 1982, pp. 863-872.
Dubois Je et al: "Friedel-Crafts Acylation of Substituted Olefins—Synthesis of Hindered Unsaturated-Ketones", Bulletin De La Societe Chimique De France, Societe Francaise De Chimie. Paris, France, No. 3-4, Jan. 1, 1984, pp. 133-138, XP009503709.
Cantrell T S et al: "Photochemical Reactions of Arenecarboxylic Acid Esters With Electron-Rich Alkenes 2 Plus 2 Cycloaddition Hydrogen Abstraction and Cycloreversion", Journal of Organic Chemistry, vol. 54, No. 1, 1989, pp. 135-139, XP002780769.
Gaudin Jean-Marc et al: "Transition metal-free addition of ketones or nitriles to 1,3-dienes.", Chemical Communications (Cambridge, England) Feb. 7, 2008, No. 5, Feb. 7, 2008, pp. 588-590, XP002780768.

(Continued)

*Primary Examiner* — Sikarl A Witherspoon
(74) *Attorney, Agent, or Firm* — Maschoff Brennan

(57) ABSTRACT

The present invention relates to new classes of odorous ketones (odorants) which are useful as fragrance or flavor materials in particular in providing coniferous, thuya, floral and/or fruity olfactory notes to perfume, aroma or deodorizing/masking compositions.

20 Claims, No Drawings

(56) References Cited

OTHER PUBLICATIONS

Coates et al.: "Regiospecific Synthesis of Trimethylsilyl Enol Ethers via Silatropic Rearrangements", Journal of the American Chemical Society, vol. 97, No. 6, Mar. 19, 1975, pp. 1619-1621, XP002780770.
El Abed et al.: "1,2-Acyl Migration from beta-Acyl-gamma-Trimethylsilyl Carbenium Ion", Tetrahedron, vol. 46, No. 17, 1990, pp. 5993-5998, XP002780771.
Engel et al.: "Clocking Tertiary Cyclopropylcarbinyl Radical Rearrangements", Journal of Organic Chemistry, vol. 62, 1997, pp. 1210-1214, XP002780772.
Hoffmann et al.: "Isolierung and Kristallstrukturanalyse eines Palladacyclobutans: Einblick in den Mechanismus der Cyclopropanierung", Angewandte Chemie, vol. 107, No. 1, 1995, pp. 73-76, XP002780773.

ODORANTS AND COMPOSITIONS COMPRISING ODORANTS

FIELD OF THE INVENTION

The present invention relates to new classes of odorous ketones which are useful as fragrance or flavor materials in particular in providing coniferous, thuya, floral and/or fruity olfactory notes to perfume, aroma or deodorizing/masking compositions and also conferring to said compositions one or more of the following advantages/properties: complex odor profile, natural impression, high volatility (influencing top notes), and/or solubility. The present invention also relates to fragrance, flavor and/or deodorizing/masking compositions comprising said new classes of odorant ketones. The present invention furthermore refers to the said odorants which can be used in the novel fragrance, flavor and/or deodorizing/masking compositions of the present invention. The present invention also refers to a method for the production of the said odorants/compounds and of the corresponding fragrance, flavor and/or deodorizing/masking compositions containing said odorants/compounds.

BACKGROUND OF THE INVENTION

Typically, many odorants that are presently utilized in the perfumery industry and/or the flavor industry are synthetic molecules. In particular, there is a high demand and need for novel odorants/compounds and/or for novel fragrance, flavor and/or deodorizing/masking compositions comprising said odorants/compounds.

For industrial applications it is beneficial if various products can be derived from one basic scaffold/raw material. It becomes even more beneficial if the raw material is exclusive in certain aspects. 2,3-Dimethylbutenes 1 and 2 are almost exclusively used for production of substituted tetralines (3) and in particular in production of Tonalid (4).

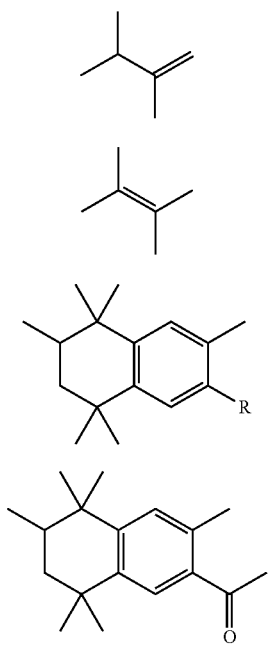

Therefore, in the course of their research and development activities, the Applicants started to develop products based on 2,3-dimethylbutenes 1 and 2 as a raw material(s) for novel odorants. It is an advantage of one or more of the embodiments of the present invention that the claimed odorants/compounds derived from 2,3-dimethybutenes can impart and/or accentuate particular olfactory notes, in particular providing coniferous, thuya, floral, and/or fruity olfactory notes to fragrance, flavor and/or deodorizing/masking compositions, and also confer to said compositions one or more of the following advantages/properties: complex odor profile, natural impression, high volatility (influencing top notes), and/or solubility.

Prior Art

Many articles in the chemistry prior art have disclosed keto compounds; whilst some of said ketones may fall within the ketones family detailed hereafter in our compounds of formula (5) or of formula (6), it remains that none of said prior art articles mention the olfactory property of the said ketones and application in perfumery or perfumed products.

SUMMARY OF THE INVENTION

This invention discloses novel fragrance, flavor and/or deodorizing/masking compositions comprising a ketone selected from compounds of formula (5) or of formula (6)

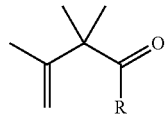

Formula (5)

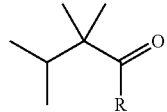

Formula (6)

wherein R is an alkyl group having from 1 to 9 carbon atoms, an alkenyl group containing only one carbon-carbon double bond and having up to 9 carbon atoms, an (substituted) aryl group having up to 9 carbon atoms, an oxo-alkyl group having up to 9 carbon atoms, an alkoxyaryl group containing up to 9 carbon atoms or a (substituted) benzyl group having up to 9 carbon atoms.

In an embodiment according to the present invention, R is methyl, ethyl, n-propyl, propyl, n-butyl, s-butyl, t-butyl, i-butyl, 2-pentyl, 3-pentyl, cyclopropyl, cyclobutyl, cyclopentyl, cyclohexyl, 1-(cyclohexylmethyl), (methoxy)methyl, (ethoxy)methyl, 1-propenyl, 1-isobutenyl, 3-butenyl, 5-(2-methylpent-2-en)yl, 4-penten-2-enyl, 4-pent-1-enyl, 4-(4-methylpent-1-en)yl, 5-(2,5-dimethylhex-2-en)yl, benzyl, phenyl, or 4-methoxyphenyl.

In an embodiment when R group contains chiral centers, the compounds of this invention can occur as stereoisomers e.g. as compounds with R or S configuration or as a mixture of thereof.

In another embodiment when R is an alkenyl group containing only one carbon-carbon double bond and having up to 9 carbon atoms, the compounds of this invention can occur as stereoisomers e.g. as compounds with Z or E configuration of the C=C bond or as a mixture of thereof.

In another embodiment the compounds of this invention can be chiral, e.g. they can occur as stereoisomeric mixtures, more specifically as mixture of enantiomers; R isomer, S isomer, a racemic mixture and/or a non-racemic mixture of R and S isomers and they can also be advantageously used in pure form or as mixtures.

DETAILED DESCRIPTION

The term "odorant" characterizing the compounds according to the present invention means that in humans it triggers an odor sensation which is preferably pleasant; it is therefore conventionally used for perfuming industrial and sanitary articles, washing agents, cleaning agents, personal hygiene products, cosmetics and the like. For the purposes of the present invention and appended claims, the term "odorant" includes "aroma substances". Aroma substances is the term usually used to designate substances which provide odor and/or flavor to foodstuffs.

The ketone compounds of formula (5) or of formula (6) may be used alone, as mixtures thereof, and/or in combination with a base material.

As used herein, the "base material" includes all known fragrance/flavor materials selected from the extensive range of natural products like: essential oils, extracts, resinoids or isolates and synthetic materials currently available, such as: hydrocarbons, alcohols, aldehydes and ketones, ethers and acetals, esters and lactones, nitriles, oximes or heterocycles, and/or in admixture with one or more ingredients or excipients/adjuvants conventionally used in conjunction with odorants in fragrance and/or flavor compositions, for example: solvents/diluents, stabilizers, carrier materials, and other auxiliary agents commonly used in the art.

The ketone compounds of formula (5) or of formula (6)—may be used in a broad range of fragrance applications, e.g. in any field of fine and functional perfumery, such as perfumes, air care products, household products, laundry products, body care products and cosmetics. The compounds can be employed in widely varying amounts, depending upon the specific application and on the nature and quantity of other odorant ingredients.

According to a preferred embodiment of the invention, the fragrance, flavor and/or deodorizing/masking composition according to the present invention contains at least one ketone compound of formula (5) or of formula (6) in quantities between 0.00001 and 99.9 wt. %, for example between 0.0001 and 95 wt. % for example between 0.001 and 25 wt. %, preferably between 0.01 and 15 wt. %, more advantageously between 0.1 and 10 wt. %, in particular between 1 and 5 wt. %, in each case relative to the entire composition. The use of more than one ketone compound according to formula (5) or formula (6) in a fragrance, flavor and/or deodorizing/masking composition according to the present invention can be particularly advantageous when the difference of the number of carbon atoms of the respective ketone of the same generic formula is between 1 and 9, for example between 1 and 5, preferably between 1 and 4, more advantageously between 1 and 3, in particular between 1 and 2. When a mixture of ketones is used, the weight ratio between the ketone present in highest weight and the ketone present in the second highest weight in the mixture is comprised between 99.9% and 50% for example between 99% and 70%, preferably between 98% and 80%, more advantageously between 98% and 90%, in particular between 98% and 95%.

According to a particularly preferred embodiment of the invention, in addition to the compound of formula (5) or of formula (6) according to the present invention, the fragrance, flavor and/or deodorizing/masking composition according to the present invention contains additional odorants, for example in a quantity of 0.1 to 99.9 wt. %, preferably 5-90 wt. %, in particular 15-70 wt. %, relative to the entire fragrance and/or flavor composition.

The compounds of formula (5) or of formula (6) as described hereinabove may be employed in a consumer product base simply by directly mixing at least one compound of formula (5) or of formula (6), or a fragrance composition comprising said compound of formula (5) or of formula (6), with the consumer product base; or they may, in an earlier step, be entrapped with an entrapment material, for example, polymers, capsules, microcapsules and/or nanocapsules, liposomes, film formers, absorbents such as active carbon or zeolites, cyclic oligosaccharides, cyclic glycourils, and mixtures of two or more thereof, or they may be chemically bonded to substrates, which are adapted to release the fragrance molecule upon application of an external stimulus such as light, enzyme, air, water or the like, and then mixed with the consumer product base.

Thus, the invention can be useful for existing methods of manufacturing a fragrance, flavor and/or deodorizing/masking composition, comprising the incorporation of a compound of formula (5) or of formula (6), as a fragrance, flavor and/or deodorizing/making ingredient, either by directly admixing the compound to the consumer product base or by admixing a fragrance, flavor and/or deodorizing/masking composition comprising said compound of formula (5) or of formula (6), which may then be mixed with a consumer product base, using conventional techniques and methods. Through the addition of an olfactory-acceptable amount of at least one compound of formula (5) or of formula (6) of the present invention as hereinabove described, the odor notes of a consumer product base can be improved, enhanced, and/or modified.

The present invention provides novel fragrance, flavor and/or deodorizing/masking compositions comprising a ketone selected from compounds of formula (5) or of formula (6)

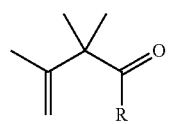

Formula (5)

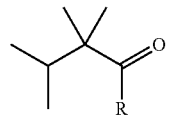

Formula (6)

wherein R is an alkyl group having from 1 to 9 carbon atoms, an alkenyl group containing only one carbon-carbon double bond and having up to 9 carbon atoms, an (substituted) aryl group having up to 9 carbon atoms, an oxo-alkyl group having up to 9 carbon atoms, an alkoxyaryl group containing up to 9 carbon atoms or a (substituted) benzyl group having up to 9 carbon atoms.

In an embodiment according to the present invention, R is methyl, ethyl, n-propyl, i-propyl, n-butyl, s-butyl, t-butyl, i-butyl, 2-pentyl, 3-pentyl, cyclopropyl, cyclobutyl, cyclopentyl, cyclohexyl, 1-(cyclohexylmethyl), (methoxy) methyl, (ethoxy)methyl, 1-propenyl, 1-isobutenyl, 3-butenyl, 5-(2-methylpent-2-en)yl, 4-penten-2-enyl, 4-pent-1-enyl, 4-(4-methylpent-1-en)yl, 5-(2,5-dimethylhex-2-en)yl, benzyl, phenyl, or 4-methoxyphenyl.

In an embodiment according to the present invention, the fragrance, flavor and/or deodorizing/masking composition comprises the compound of formula (5) or of formula (6) which is selected from

| Structure | Chemical name |
|---|---|
| 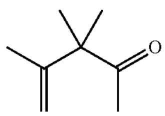 | 3,3,4-trimethylpent-4-en-2-one |
| 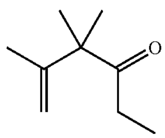 | 4,4,5-trimethylhex-5-en-3-one |
| 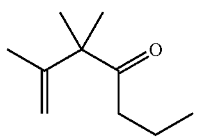 | 2,3,3-trimethylhept-1-en-4-one |
| 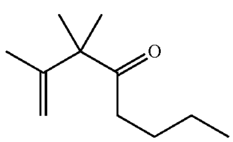 | 2,3,3-trimethyloct-1-en-4-one |
| 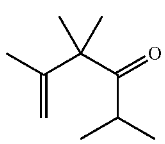 | 2,4,4,5-tetramethylhex-5-en-3-one |
| 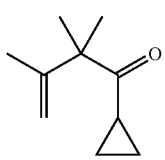 | 1-cyclopropyl-2,2,3-trimethylbut-3-en-1-one |
| 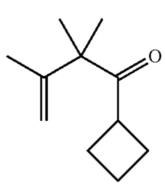 | 1-cyclobutyl-2,2,3-trimethylbut-3-en-1-one |
| 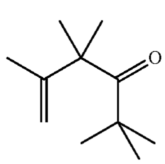 | 2,2,4,4,5-pentamethylhex-5-en-3-one |
| 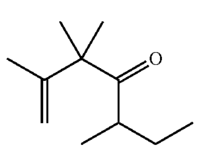 | 2,3,3,5-tetramethylhept-1-en-4-one |

-continued

| Structure | Chemical name |
|---|---|
| 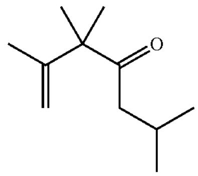 | 2,3,3,6-tetramethylhept-1-en-4-one |
| 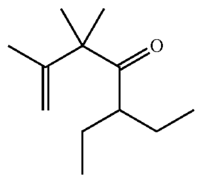 | 5-ethyl-2,3,3-trimethylhept-1-en-4-one |
| 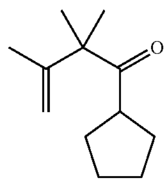 | 1-cyclopentyl-2,2,3-trimethylbut-3-en-1-one |
| 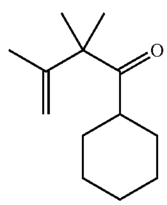 | 1-cyclohexyl-2,2,3-trimethylbut-3-en-1-one |
| 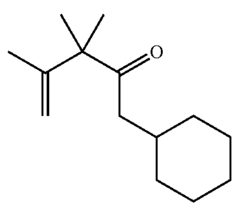 | 1-cyclohexyl-2,2,3-trimethylpent-4-en-2-one |
| 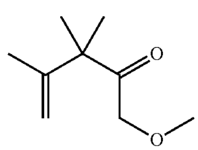 | 1-methoxy-3,3,4-trimethylpent-4-en-2-one |
| 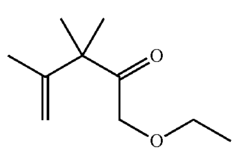 | 1-ethoxy-3,3,4-trimethylpent-4-en-2-one |
| 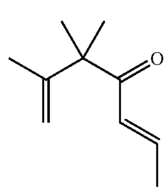 | 2,3,3-trimethylhepta-1,5-dien-4-one |

-continued

| Structure | Chemical name |
|---|---|
| 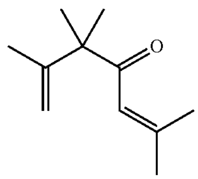 | 2,3,3,6-tetramethylhepta-1,5-dien-4-one |
| 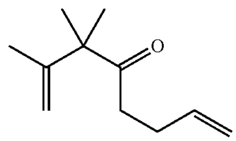 | 2,3,3-trimethylocta-1,7-dien-4-one |
| 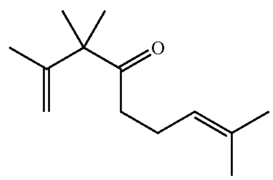 | 2,3,3,8-tetramethylnona-1,7-dien-4-one |
| 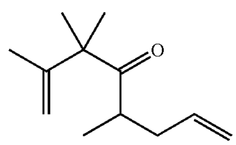 | 2,3,3,5-tetramethylocta-1,7-dien-4-one |
| 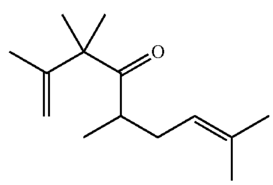 | 2,3,3,5,8-pentamethylnona-1,7-dien-4-one |
| 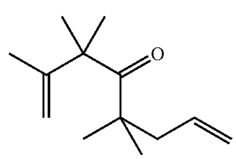 | 2,3,3,5,5-pentamethylocta-1,7-dien-4-one |
| 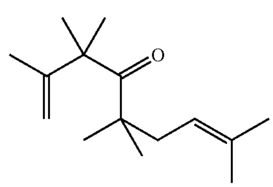 [SMILES: C=C(C)C(C)(C)C(=O)C(C)(C)CC=C(C)C] | 2,3,3,5,5,8-hexamethylnona-1,7-dien-4-one |
| 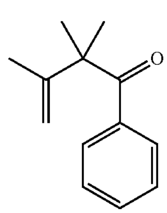 | 2,2,3-trimethyl-1-phenylbut-3-en-1-one |

-continued
| Structure | Chemical name |
|---|---|
| 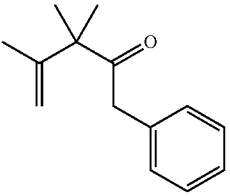 | 3,3,4-trimethyl-1-phenylpent-4-en-2-one |
| 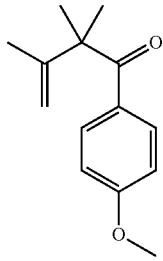 [SMILES: C=C(C)C(C)(C)C(=O)c1ccc(OC)cc1] | 1-(4-methoxyphenyl)-2,2,3-trimethylbut-3-en-1-one |
| 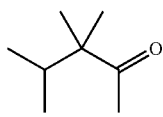 | 3,3,4-trimethylpentan-2-one |
| 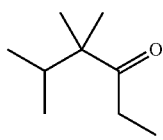 | 4,4,5-trimethylhexan-3-one |
| 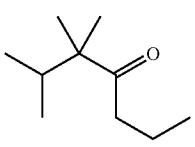 | 2,3,3-trimethylheptan-4-one |
| 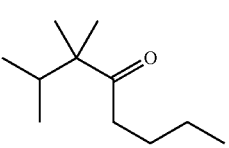 | 2,3,3-trimethyloctan-4-one |
| 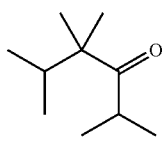 | 2,4,4,5-tetramethylhexan-3-one |
| 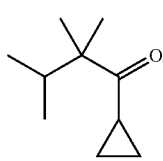 | 1-cyclopropyl-2,2,3-trimethylbutan-1-one |
| 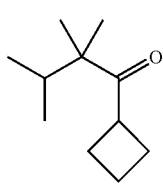 | 1-cyclobutyl-2,2,3-trimethylbutan-1-one |

-continued

| Structure | Chemical name |
|---|---|
| 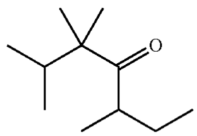 | 2,3,3,5-tetramethylheptan-4-one |
| 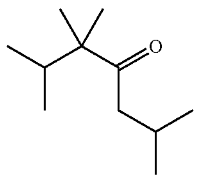 | 2,3,3,6-tetramethylheptan-4-one |
| 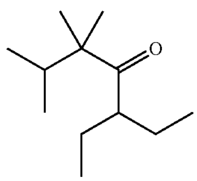 | 5-ethyl-2,3,3-trimethylheptan-4-one |
| 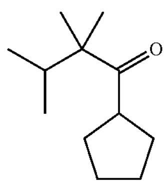 | 1-cyclopentyl-2,2,3-trimethylbutan-1-one |
| 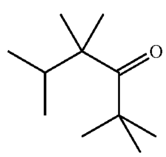 | 2,2,4,4,5-pentamethylhexan-3-one |
| 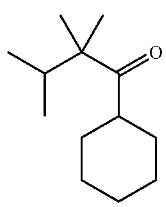 | 1-cyclohexyl-2,2,3-trimethylbutan-1-one |
| 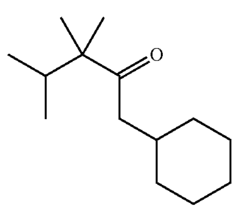 | 1-cyclohexyl-3,3,4-trimethylpentan-2-one |
| 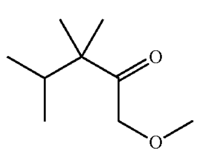 | 1-methoxy-3,3,4-trimethylpentan-2-one |
| 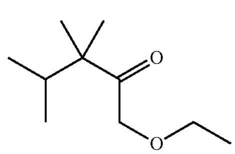 | 1-ethoxy-3,3,4-trimethylpentan-2-one |

-continued

| Structure | Chemical name |
|---|---|
| 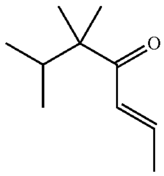 | 5,5,6-trimethylhept-2-en-4-one |
| 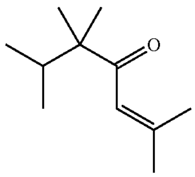 | 2,5,5,6-trimethylhept-2-en-4-one |
| 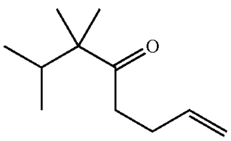 | 2,3,3-trimethyloct-7-en-4-one |
| 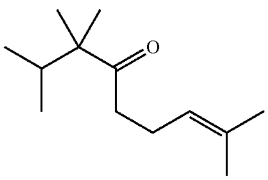 | 2,3,3,8-tetramethylnon-7-en-4-one |
| 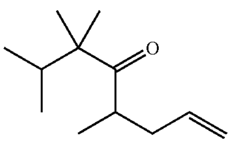 | 2,3,3,5-tetramethyloct-7-en-4-one |
| 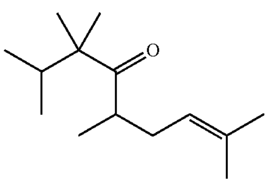 | 2,3,3,5,8-pentamethylnon-7-en-4-one |
| 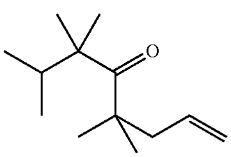 | 2,3,3,5,5-pentamethyloct-7-en-4-one |
| 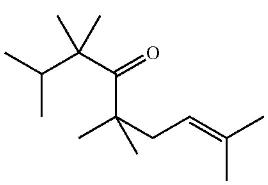 [SMILES: CC(C)=CCC(C)(C)C(=O)C(C)(C)C(C)C] | 2,3,3,5,5,8-hexamethylnon-7-en-4-one |
| 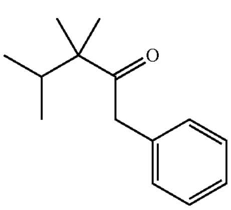 | 3,3,4-trimethyl-1-phenylpentan-2-one |

| Structure | Chemical name |
|---|---|
| 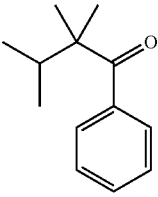 | 2,2,3-trimethyl-1-phenylbutan-1-one |
| 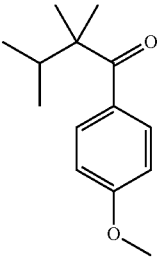 [SMILES: COc1ccc(C(=O)C(C)(C)C(C)C)cc1] | 1-(4-methoxyphenyl)-2,2,3-trimethylbutan-1-one | and/or a mixture of two or more of the said compounds.

The Applicants have also discovered that, from an olfactory perspective, the compounds of formula (5) or of formula (6) have a distinctly coniferous, thuya, floral and/or fruity profile that lends itself directly to use in herbaceous or coniferous compositions such as for example pine, fir, eucalyptus, mint, or lavender or fruity compositions such as for example plum, apple or lychee. They are also more versatile, with easily recognizable applications toward myrtle, rosemary, as well as notes like for instance citrus, rose, gardenia and/or jasmine. Furthermore, compared to other odorants like e.g. verdyl propionate, the compounds of formula (5) or of formula (6) have greater diffusivity and presence. They have greater stability and volatility in various application media in particular basic media.

Ketones

In a particular embodiment according to the present invention, the compounds of formula (5) and/or of formula (6) useful in the perfume, aroma and/or deodorizing/masking compositions of the present invention are selected from

| Structure | Chemical name |
|---|---|
| 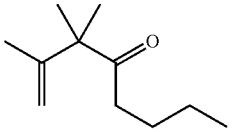 | 2,3,3-trimethyloct-1-en-4-one |
| 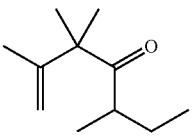 | 2,3,3,5-tetramethylhept-1-en-4-one |
| 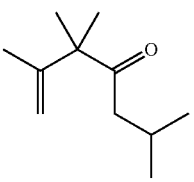 | 2,3,3,6-tetramethylhept-1-en-4-one |
| 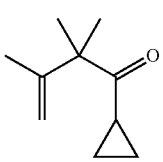 | 1-cyclopropyl-2,2,3-trimethylbut-3-en-1-one |

-continued

| Structure | Chemical name |
|---|---|
| 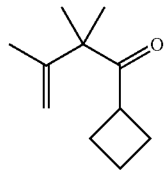 | 1-cyclobutyl-2,2,3-trimethylbut-3-en-1-one |
| 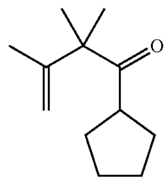 | 1-cyclopentyl-2,2,3-trimethylbut-3-en-1-one |
| 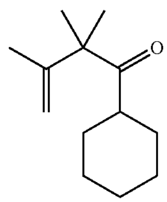 | 1-cyclohexyl-2,2,3-trimethylbut-3-en-1-one |
| 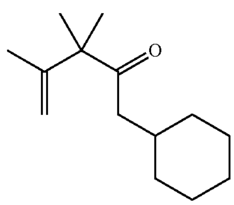 | 1-cyclohexyl-3,3,4-trimethylpent-4-en-1-one |
| 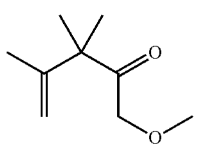 | 1-methoxy-3,3,4-trimethylpent-4-en-2-one |
| 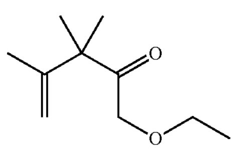 | 1-ethoxy-3,3,4-trimethylpent-4-en-2-one |
| 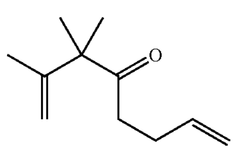 | 2,3,3-trimethylocta-1,7-dien-4-one |
| 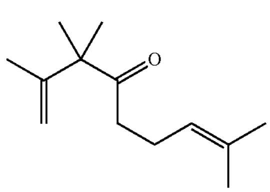 | 2,3,3,8-tetramethylnona-1,7-dien-4-one |
| 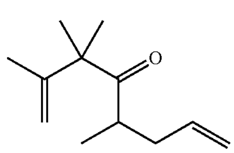 | 2,3,3,5-tetramethylocta-1,7-dien-4-one |

-continued

| Structure | Chemical name |
|---|---|
| 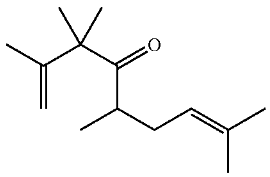 | 2,3,3,5,8-pentamethylnona-1,7-dien-4-one |
| 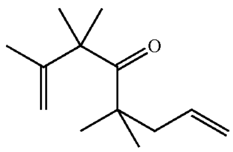 | 2,3,3,5,5-pentamethylocta-1,7-dien-4-one |
| 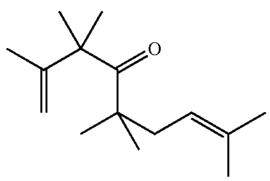 [SMILES: C=C(C)C(C)(C)C(=O)C(C)(C)CC=C(C)C] | 2,3,3,5,5,8-hexamethylnona-1,7-dien-4-one |
| 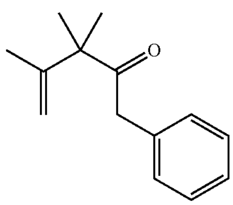 | 3,3,4-trimethyl-1-phenylpent-4-en-2-one |
| 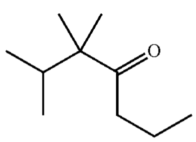 | 2,3,3-trimethylheptan-4-one |
| 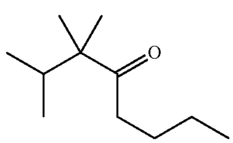 | 2,3,3-trimethyloctan-4-one |
| 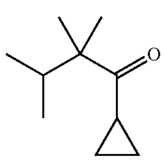 | 1-cyclopropyl-2,2,3-trimethylbutan-1-one |
| 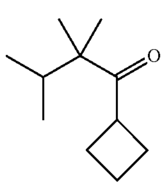 | 1-cyclobutyl-2,2,3-trimethylbutan-1-one |
| 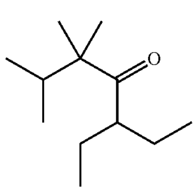 | 5-ethyl-2,3,3-trimethylheptan-4-one |

| Structure | Chemical name |
|---|---|
| 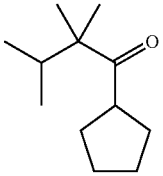 | 1-cyclopentyl-2,2,3-trimethylbutan-1-one |
| 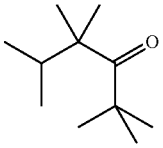 | 2,2,4,4,5-pentamethylhexan-3-one |
| 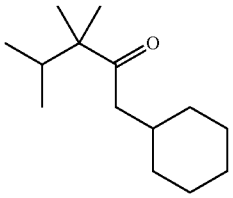 | 1-cyclohexyl-3,3,4-trimethylpentan-2-one |
| 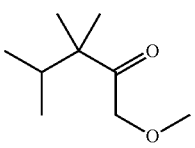 | 1-methoxy-3,3,4-trimethylpentan-2-one |
| 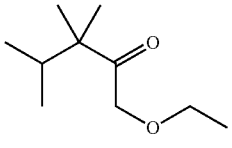 | 1-ethoxy-3,3,4-trimethylpentan-2-one |
| 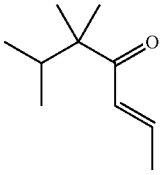 | 5,5,6-trimethylhept-2-en-4-one |
| 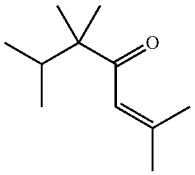 | 2,5,5,6-tetramethylhept-2-en-4-one |
| 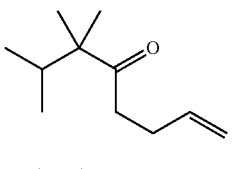 | 2,3,3-trimethyloct-7-en-4-one |
| 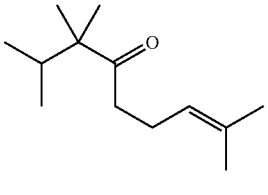 | 2,3,3,8-tetramethylnon-7-en-4-one |

| Structure | Chemical name |
|---|---|
| 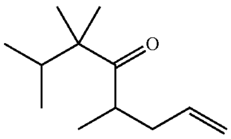 | 2,3,3,5-tetramethyloct-7-en-4-one |
| 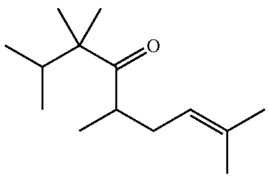 | 2,3,3,5,8-pentamethylnon-7-en-4-one |
| 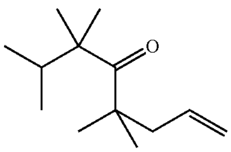 | 2,3,3,5,5-pentamethyloct-7-en-4-one |
| 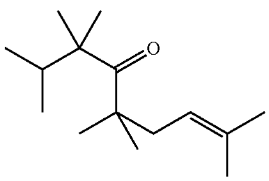 [SMILES: CC(C)=CCC(C)(C)C(=O)C(C)(C)C(C)C] | 2,3,3,5,5,8-hexamethylnon-7-en-4-one |
| 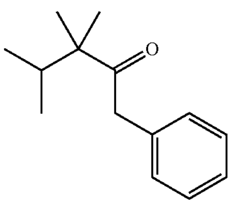 | 3,3,4-trimethyl-1-phenylpentan-2-one |
| 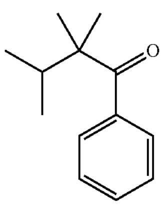 | 2,2,3-trimethyl-1-phenylbutan-1-one |
| | 1-(4-methoxyphenyl)-2,2,3-trimethylbutan-1-one | and/or a mixture of two or more of the said compounds.

Preparation

In a preferred embodiment according to the present invention, the compounds of formula (5) and/or of formula (6) can advantageously be prepared from 2,3-dimethylbutene(s) as illustrated hereafter.

2,3-Dimethylbutenes

The 2,3-dimethylbutenes compounds according to the present invention can be selected from 2,3-dimethyl-1-butene, 2,3-dimethyl-2-butene, or a mixture thereof; preferably from 2,3-dimethyl-2-butene or from a mixture of 2,3-dimethyl-2-butene and 2,3-dimethyl-1-butene.

Optional Isomerisation Step

In an embodiment according to the present invention, an isomerisation step is preferably performed in order to convert 2,3-dimethyl-1-butene into 2,3-dimethyl-2-butene. This isomerisation step is preferably performed for example when the starting material is 2,3-dimethyl-1-butene or when the starting material is a mixture of 2,3-dimethyl-2-butene and 2,3-dimethyl-1-butene having a content of 2,3-dimethyl-1-butene superior to the content of 2,3-dimethyl-2-butene. Any appropriate olefin isomerisation process can be used; as illustrative and non-restricting examples, base-catalysed and/or acid-catalysed isomerisation process can advantageously be used. In an embodiment according to the present invention, an ion-exchange resin acid catalyst, e.g. an Amberlyst catalyst in the acid form is advantageously used.

Acylation Synthesis Step

Thus, in an embodiment of the present invention, the 2,3-dimethylbutene(s) are subjected to an acylation synthesis step to form the compounds of formula (5) which can be represented by the following formula

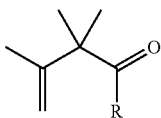

5 wherein R is an alkyl group having from 1 to 9 carbon atoms, an alkenyl group containing only one carbon-carbon double bond and having up to 9 carbon atoms, an (substituted) aryl group having up to 9 carbon atoms, an oxo-alkyl group having up to 9 carbon atoms, an alkoxyaryl group containing up to 9 carbon atoms or a (substituted) benzyl group having up to 9 carbon atoms.

In an embodiment of the present invention, the product is obtained by reacting 2,3-dimethylbutene(s) with acyl anhydride or acyl chloride, preferably followed by usual workup (e.g. aqueous wash, removal of unreacted reactants and/or solvents and distillation). An acceptable alternative way of describing the said compound of formula (5) is 1-substituted, 3,3,4-trimethyl-pent-4-en-2-one wherein the substituent in position 1 is selected from methyl, ethyl, n-propyl, i-propyl, n-butyl, s-butyl, t-butyl, i-butyl, 2-pentyl, 3-pentyl, cyclopropyl, cyclobutyl, cyclopentyl, cyclohexyl, 1-(cyclohexylmethyl), (methoxy)methyl, (ethoxy)methyl, 1-propenyl, 1-isobutenyl, 3-butenyl, 5-(2-methylpent-2-en)yl, 4-penten-2-enyl, 4-pent-1-enyl, 4-(4-methylpent-1-en)yl, 5-(2,5-dimethylhex-2-en)yl, benzyl, phenyl, 4-methoxyphenyl.

Any appropriate acylation process leading to compound of formula (5) can be used; as illustrative and non-restricting examples, the acylation is performed in the presence of 2,3-dimethylbutene(s) and a carboxylic acid anhydride, for example acetic anhydride. This process step can advantageously be operated in the presence of a Lewis or Brønsted acid catalyst, for example zinc chloride, methylsulfonic acid, trifluoromethylsulfonic acid, etc. This process step can advantageously be operated either neat or with the use of a suitable aprotic, polar solvent (e.g. dichloromethane).

In an embodiment of the present invention, the fragrance, flavor and/or deodorizing/masking compositions, wherein the ketone(s) is(are) prepared by subjecting 2,3-dimethylbutene(s) to the acylation reaction step, also comprise, in addition to the ketone(s), at least one of the side product(s) obtained during the said acylation reaction step. In an embodiment according to the present invention, the acylation step is preferably followed by an alkylation step; e.g. the 2,3-dimethylbutene(s) are subjected to an acylation synthesis step to form the compounds of formula (5a) as represented by the following formula (5a, i.e. wherein R=CH$_3$)

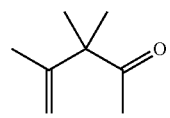

5a which is then converted into compounds of formula (5b) as represented by the following formula

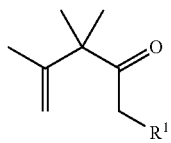

5b wherein R$^1$ is selected from an alkyl group having from 1 to 8 carbon atoms, an alkenyl group containing only one carbon-carbon double bond and having up to 8 carbon atoms, an oxo-alkyl group having up to 8 carbon atoms, or a (substituted) benzyl group having up to 8 carbon atoms.

Compound of the formula (5b) which can be obtained either by subjecting 2,3-dimethylbutene(s) to an acylation synthesis step to form directly the compounds of formula (5b) or by subjecting compounds of formula (5a) to an alkylation step can be further alkylated to form compound of formula (5c).

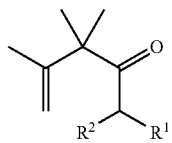

5c wherein R$^1$ is selected from an alkyl group having from 1 to 7 carbon atoms, an alkenyl group containing only one carbon-carbon double bond and having up to 7 carbon atoms, an aryl group having up to 7 carbon atoms, an oxo-alkyl group having up to 7 carbon atoms, an alkoxyaryl group containing up to 7 carbon atoms or a (substituted) benzyl group having up to 7 carbon atoms, and R$^2$ is selected from an alkyl group having from 1 to 7 carbon atoms, an alkenyl group containing only one carbon-carbon double bond and having up to 7 carbon atoms, an (substituted) aryl group having up to 7 carbon atoms, an oxo-alkyl group having up to 7 carbon atoms, an alkoxyaryl group containing up to 7 carbon atoms or a (substituted) benzyl group having up to 7 carbon atoms and the sum of carbon atoms present in radicals R$^1$ and R$^2$ is not more than 8.

Compound of the formula (5c) which can be obtained either by subjecting 2,3-dimethylbutene(s) to an acylation synthesis step to form directly the compounds of formula (5c) or by subjecting compounds of formula (5b) to an alkylation step or by subjecting compound (5a) to a double alkylation step can be further alkylated to form compound of formula (5d).

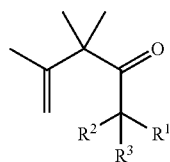

5d wherein $R^1$ an alkyl group having from 1 to 6 carbon atoms, an alkenyl group containing only one carbon-carbon double bond and having up to 6 carbon atoms, an aryl group having up to 6 carbon atoms, an oxo-alkyl group having up to 6 carbon atoms, and $R^2$ is selected from an alkyl group having from 1 to 6 carbon atoms, an alkenyl group containing only one carbon-carbon double bond and having up to 6 carbon atoms, or an oxo-alkyl group having up to 6 carbon atoms, $R^3$ is selected from an alkyl group having from 1 to 6 carbon atoms, an alkenyl group containing only one carbon-carbon double bond and having up to 6 carbon atoms, or an oxo-alkyl group having up to 6 carbon atoms, and the sum of carbon atoms present in radicals $R^1$, $R^2$ and $R^2$ is not more than 8.

When compounds of formula (5c) and (5d) have at least two of the $R^1$, $R^2$ or $R^3$ groups identical, the introduction of these identical groups can be performed in a single alkylation step.

An advantage of the acylation step of the synthesis process of the present invention—when 2,3-dimethyl-2-butene is the starting material—is that it can tolerate the presence of 2,3-dimethyl-1-butene. Consequently, whilst the present invention preferentially uses pure 2,3-dimethyl-2-butene for the acylation step, it can also advantageously tolerate as starting materials molar ratios of 2,3-dimethyl-2-butene to 2,3-dimethyl-1-butene which is lower than 99%, for example lower than 95% said molar ratio is preferably higher than 50%, for example higher than 75%, or even higher than 85%.

In an alternative embodiment according to the present invention, the acylation step is preferably followed by an aldol condensation step; e.g. the 2,3-dimethylbutene(s) are subjected to an acylation synthesis step to form the compounds of formula (5a) as represented by the following formula (5a, i.e. wherein R=CH₃)

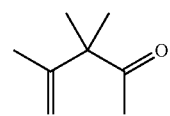

5a which is then converted into compounds of formula (5e) as represented by the following formula

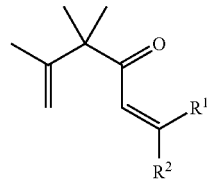

5e wherein $R^1$ is selected from hydrogen, an alkyl group having from 1 to 7 carbon atoms, an aryl group having up to 7 carbon atoms, an oxo-alkyl group having up to 7 carbon atoms, an alkoxyaryl group containing up to 7 carbon atoms or a (substituted) benzyl group having up to 7 carbon atoms, and $R^2$ is selected from hydrogen, an alkyl group having from 1 to 7 carbon atoms, an (substituted) aryl group having up to 7 carbon atoms, an oxo-alkyl group having up to 7 carbon atoms, an alkoxyaryl group containing up to 7 carbon atoms or a (substituted) benzyl group having up to 7 carbon atoms and the sum of carbon atoms present in radicals $R^1$ and $R^2$ is not more than 7.

In an embodiment of the present invention, compound of the formula (5b) which can be obtained either by subjecting 2,3-dimethylbutene(s) to an acylation synthesis step to form directly the compounds of formula (5b) or by subjecting compounds of formula (5a) to an alkylation step can be subjected to an aldol condensation step to form compound of formula (5f).

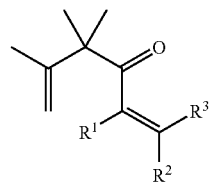

5f wherein $R^1$ is selected from an alkyl group having from 1 to 7 carbon atoms, an aryl group having up to 7 carbon atoms, an oxo-alkyl group having up to 7 carbon atoms, an alkoxyaryl group containing up to 7 carbon atoms or a (substituted) benzyl group having up to 7 carbon atoms, and $R^2$ is selected from hydrogen, an alkyl group having from 1 to 6 carbon atoms, an (substituted) aryl group having up to 6 carbon atoms, an oxo-alkyl group having up to 6 carbon atoms, and $R^3$ is selected from hydrogen, an alkyl group having from 1 to 6 carbon atoms, an (substituted) aryl group having up to 6 carbon atoms, an oxo-alkyl group having up to 6 carbon atoms, and the sum of carbon atoms present in radicals $R^1$ and $R^2$ and $R^3$ is not more than 7.

In an embodiment according to the present invention, the acylation step is preferably followed by hydrogenation step and an alkylation step; e.g. the 2,3-dimethylbutene(s) are subjected to an acylation synthesis step followed by hydrogenation synthesis step to form the compounds of formula (6a) as represented by the following formula (6a, i.e. wherein R=CH₃)

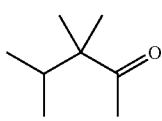

6a which is then converted into compounds of formula (6b) as represented by the following formula

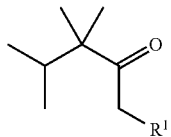

6b wherein R¹ is selected from an alkyl group having from 1 to 8 carbon atoms, an alkenyl group containing only one carbon-carbon double bond and having up to 8 carbon atoms, an oxo-alkyl group having up to 8 carbon atoms, or a (substituted) benzyl group having up to 8 carbon atoms.

In an embodiment of the present invention, compound of the formula (5b) which can be obtained either by subjecting 2,3-dimethylbutene(s) to an acylation synthesis step to form directly the compounds of formula (5b) or by subjecting compounds of formula (6a) to an alkylation step can be further alkylated to form compound of formula (6c).

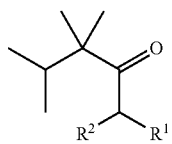

6c wherein R¹ is selected from an alkyl group having from 1 to 7 carbon atoms, an alkenyl group containing only one carbon-carbon double bond and having up to 7 carbon atoms, an aryl group having up to 7 carbon atoms, an oxo-alkyl group having up to 7 carbon atoms, an alkoxyaryl group containing up to 7 carbon atoms or a (substituted) benzyl group having up to 7 carbon atoms, and R² is selected from an alkyl group having from 1 to 7 carbon atoms, an alkenyl group containing only one carbon-carbon double bond and having up to 7 carbon atoms, an (substituted) aryl group having up to 7 carbon atoms, an oxo-alkyl group having up to 7 carbon atoms, an alkoxyaryl group containing up to 7 carbon atoms or a (substituted) benzyl group having up to 7 carbon atoms and the sum of carbon atoms present in radicals R¹ and R² is not more than 8

In an embodiment of the present invention, compound of the formula 6c which can be obtained either by subjecting 2,3-dimethylbutene(s) to an acylation synthesis step to form directly the compounds of formula (6c) or by subjecting compounds of formula (6b) to an alkylation step or by subjecting compound (6a) to a double alkylation step can be further alkylated to form compound of formula (6d).

6d wherein R¹ an alkyl group having from 1 to 6 carbon atoms, an alkenyl group containing only one carbon-carbon double bond and having up to 6 carbon atoms, an aryl group having up to 6 carbon atoms, an oxo-alkyl group having up to 6 carbon atoms, and R² is selected from an alkyl group having from 1 to 6 carbon atoms, an alkenyl group containing only one carbon-carbon double bond and having up to 6 carbon atoms, or an oxo-alkyl group having up to 6 carbon atoms, R³ is selected from an alkyl group having from 1 to 6 carbon atoms, an alkenyl group containing only one carbon-carbon double bond and having up to 6 carbon atoms, or an oxo-alkyl group having up to 6 carbon atoms, and the sum of carbon atoms present in radicals R¹, R² and R² is not more than 8

When compounds of formula (6c) and (6d) have at least two of the R¹, R² or R³ groups identical, the introduction of these identical groups can be performed in a single alkylation step.

In an embodiment according to the present invention, the acylation step followed by a hydrogenation step is preferably followed by an aldol condensation step; e.g. the 2,3-dimethylbutene(s) are subjected to an acylation synthesis step followed by a hydrogenation step to form the compounds of formula (6a) as represented by the following formula (6a, i.e. wherein R=CH₃)

6a which is then converted into compounds of formula (6e) as represented by the following formula

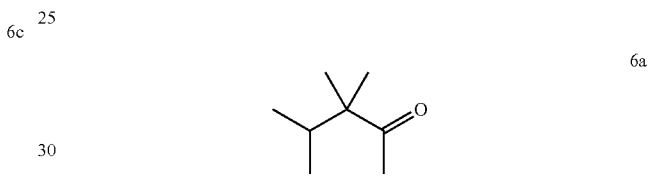

6e wherein R¹ is selected from hydrogen, an alkyl group having from 1 to 7 carbon atoms, an aryl group having up to 7 carbon atoms, an oxo-alkyl group having up to 7 carbon atoms, an alkoxyaryl group containing up to 7 carbon atoms or a (substituted) benzyl group having up to 7 carbon atoms, and R² is selected from hydrogen, an alkyl group having from 1 to 7 carbon atoms, an (substituted) aryl group having up to 7 carbon atoms, an oxo-alkyl group having up to 7 carbon atoms, an alkoxyaryl group containing up to 7 carbon atoms or a (substituted) benzyl group having up to 7 carbon atoms and the sum of carbon atoms present in radicals R¹ and R² is not more than 7.

In an embodiment according to the present invention, compound of the formula (6b) which can be obtained either by subjecting 2,3-dimethylbutene(s) to an acylation synthesis step to form directly the compounds of formula (6b) or by subjecting compounds of formula (6a) to an alkylation step can be subjected to an aldol condensation step to form compound of formula (6f).

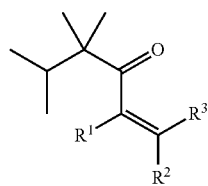

wherein R¹ is selected from an alkyl group having from 1 to 7 carbon atoms, an aryl group having up to 7 carbon atoms, an oxo-alkyl group having up to 7 carbon atoms, an alkoxyaryl group containing up to 7 carbon atoms or a (substituted) benzyl group having up to 7 carbon atoms, and R² is selected from hydrogen, an alkyl group having from 1 to 6 carbon atoms, an (substituted) aryl group having up to 6 carbon atoms, an oxo-alkyl group having up to 6 carbon atoms, and R³ is selected from hydrogen, an alkyl group having from 1 to 6 carbon atoms, an (substituted) aryl group having up to 6 carbon atoms, an oxo-alkyl group having up to 6 carbon atoms, and the sum of carbon atoms present in radicals R¹ and R² and R³ is not more than 7.

The synthesis of ketones (5) and (6) can be thus advantageously realized according to the following schemes:

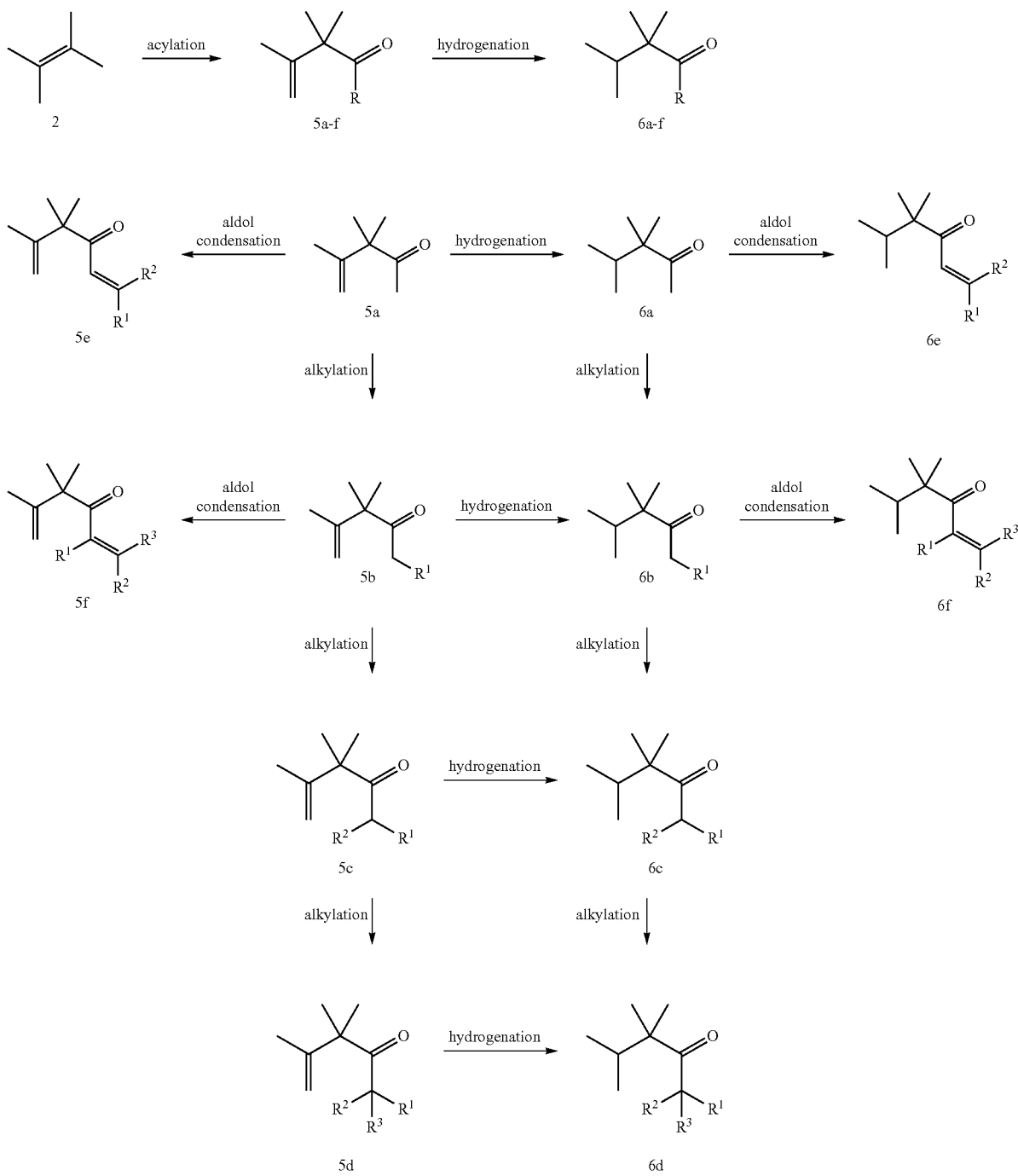

Any appropriate alkylation process leading to compounds of formula 5b-d and 6b-d respectively can be used; as illustrative and non-restricting examples, the alkylation is performed in the presence of the products of acylation of 2,3-dimethylbutenes with the general structure 5 or 6 and an alkyl halide or alkyl sulfate (methyl iodide, dimethyl sulfate, etc) in the presence of a base (potassium hydroxide, potassium tertbutoxide, etc).

Any appropriate aldol condensation process leading to compounds of formula 5e-f and 6e-f respectively can be used; as illustrative and non-restricting examples, the aldol condensation is performed in the presence of the products of acylation of 2,3-dimethylbutenes with the general structure 5 or 6 and an aldehyde or ketone in the presence of a base (potassium hydroxide, potassium tertbutoxide, etc) or in the presence of an acid (hydrochloric acid, sulfuric acid etc.).

The use of more than one ketone compound according to formula (5) or formula (6) as described herein above in a fragrance, flavor and/or deodorizing/masking composition according to the present invention can be particularly advantageous when the difference of the number of carbon atoms of the respective ketone of the same generic formula is between 1 and 9, for example between 1 and 5, preferably between 1 and 4, more advantageously between 1 and 3, in particular between 1 and 2. When a mixture of ketones is used, the weight ratio between the ketone present in highest weight and the ketone present in the second highest weight in the mixture is comprised between 99.9% and 50% for example between 99% and 70%, preferably between 98% and 80%, more advantageously between 98% and 90%, in particular between 98% and 95%.

According to an embodiment of the invention, the fragrance, flavor and/or deodorizing/masking composition according to the present invention contains at least one ketone compound of formula (5) or of formula (6) as described herein above in quantities between 0.00001 and 99.9 wt. %, for example between 0.0001 and 95 wt. %, for example between 0.001 and 25 wt. %, preferably between 0.01 and 15 wt. %, more advantageously between 0.1 and 10 wt. %, in particular between 1 and 5 wt. %, in each case relative to the entire composition.

According to a preferred embodiment of the invention, the fragrance, flavor and/or deodorizing/masking composition according to the present invention contains at least one ketone compound according to formula (5) as previously described and at least one corresponding ketone compound of formula (6) as previously described [i.e. the ketone having the same radical R], in quantities between 0.00001 and 99.9 wt. %, for example between 0.0001 and 95 wt. %, for example between 0.001 and 25 wt. %, preferably between 0.01 and 15 wt. %, more advantageously between 0.1 and 10 wt. %, in particular between 1 and 5 wt. %, in each case relative to the entire composition.

According to a particularly preferred embodiment of the invention, in addition to the compound of formula (5) or of formula (6) as described herein above, the fragrance, flavor and/or deodorizing/masking composition according to the present invention contains additional odorants, for example in a quantity of 0.1 to 99.9 wt. %, preferably 5-90 wt. %, in particular 15-70 wt. %, relative to the entire fragrance and/or flavor composition.

In an embodiment of the present invention, the claimed fragrance, flavor and/or deodorizing/masking composition is advantageously used as a perfumery composition. Perfumery compositions according to the present invention generally include a perfume, a cologne, an eau du toilette, and/or an eau de parfum. In an embodiment of the present invention, the claimed fragrance, flavor and/or deodorizing/masking composition is advantageously used in a cosmetic formulation, a personal care product, a cleansing product, a fabric softener, and/or air freshener, and the like. Furthermore, it is within the purview of embodiments of the invention that the novel fragrance, flavor and/or deodorizing/masking composition(s) and/or (novel) compound(s) of formula (5) or of formula (6) described herein may be integrated into building materials, wall and floor coverings, vehicle components, and the like.

In general, in addition to the novel odorant and/or fragrance, flavor and/or deodorizing/masking compositions described herein, suitable fragrance, flavor or deodorizing compositions may advantageously include conventional ingredients such as, for example, solvents, carriers, stabilizers, emulsifiers, moisturizers, dispersants, diluents, thickeners, thinners, other odorants, and/or adjuvants, and the like.

The compounds of formula (5) and/or (6) combine with numerous known natural or synthetic fragrance, flavor and/or deodorizing/masking materials, whereby the range of the natural ingredients can embrace not only readily-volatile but also semi-volatile and slightly-volatile components and the range of the synthetic ingredients can embrace representatives from many classes of substances, as will be evident from the following nonlimiting compilation:

Natural products such as:

Ajowan oil, Amyris oil, Armoise oil, Artemisia oil, Basil oil, Bees wax absolute, Bergamot oil, Birch tar oil, Black pepper oil, Black pepper oleoresin, Camphor oil, Cananga oil, Caraway oil, Cardamom oil, Carrot seed oil, Castoreum absolute, Cedar leaf oil, Cedarwood oil, Celery seed oil, Chamomile oil, Cinnamon bark oil, Cinnamon leaf oil, Cistus absolute, Cistus oil, Citronella oil, Citronella terpenes, Clary sage oil, Clove oil rectified, Cognac oil white, Coriander seed oil, Cumin seed oil, Cypress oil, Davana oil, Dill seed oil, Elemi oil, Elemi resinoid, Eucalyptus oil, Fir needle oil, Galbanum oil, Geranium oil, Ginger oil Indian, Grapefruit oil, Guaiacwood oil, Gurjun balsam, Jasmin absolute, Jatamansi oil, Juniper berry oil, Juniper leaf oil, Kachur oil, Labdanum absolute, Labdanum resinoid, Lavender oil, Lemon oil, Lemon oil terpenes, Lemongrass oil, Lime oil, Litsea cubeba oil, Litsea cubeba terpenes, Lobhan choya resinoid, Mandarin oil, Mentha arvenis oil, Mentha citrata oil, Mimosa absolute, Myrrh resinoid, Nagarmotha oil, Nutmeg oil, Oakmoss absolute, Oakmoss resinoid, Olibanum oil, Olibanum resinoid, Orange oil, Origanum oil, Palma rosa oil, Patchouli oil, Peppermint oil, Peru Balsam resinoid, Petitgrain oil, Pine needle oil, Pink pepper oil, Rose absolut, Rose oil, Rosemary oil, Sandalwood oil, Seaweed absolute, Spearmint oil, Sugandh kokila oil, Sugandh mantri oil, Tagete oil, Tolu Balsam resinoid, Tuberose absolute, Turmeric oil, Turpentine oil, Valerian oil, Vetiver oil, Vetiver terpenes. Synthetic raw materials for instance:

Esters such as: Aldehyde C16, Allyl amyl glycolate, Allyl caproate, Allyl cyclohexyl propionate, Allyl heptoate, Allyl phenoxy acetate, Amyl acetate iso, Amyl benzoate, Amyl butyrate, Amyl caproate, Amyl cinnamate, Amyl isovalerate, Amyl phenyl acetate, Amyl propionate, Amyl salicylate iso, Amyris acetate, Anisyl acetate, Benzyl acetate, Benzyl benzoate, Benzyl butyrate, Benzyl cinnamate, Benzyl formate, Benzyl isobutyrate, Benzyl isoeugenol, Benzyl propionate, Benzyl salicylate, Benzyl tiglate, Butyl acetate, Butyl butyrate, Butyl butyryl lactate, Caryophyllene acetate, Cedryl acetate, Cinnamyl acetate, Cinnamyl butyrate, Cis-3-hexenyl acetate, Cis-3-hexenyl benzoate, Cis-3-hexenyl caproate, Cis-3-hexenyl formate, Cis-3-hexenyl isobutyrate, Cis-3-hexenyl-2-methyl butyrate, Cis-3-hexenyl propionate, Cis-3-hexenyl salicylate, Cis-3-hexenyl tiglate, Citronellyl acetate, Citronellyl butyrate, Citronellyl formate, Citronellyl isobutyrate, Citronellyl propionate, Citronellyl tiglate, Cyclabute, Cyclogalbanate, Cyclohexyl ethyl acetate, Decyl acetate, Dibutyl phthalate, Diethyl malonate, Diethyl phthalate, Dihydromyrcenyl acetate, Dimethyl octanyl acetate, Dimethyl phenyl ethyl carbinyl acetate, Dioctyl adipate, Dioctyl phthalate, Dimethyl benzyl carbinyl acetate, Dimethyl benzyl carbinyl butyrate, Ethyl linalyl acetate, Ethyl 2-methyl butyrate, Ethyl 3-phenyl propionate, Ethyl acetate, Ethyl acetoacetate, Ethyl benzoate, Ethyl butyrate, Ethyl caprate C10, Ethyl caproate C6, Ethyl caprylate C8, Ethyl cinnamate, Ethyl heptoate, Ethyl hexyl acetate, Ethyl isobutyrate, Ethyl laurate, Ethyl pelargonate, Ethyl phenoxy acetate, Ethyl phenyl acetate, Ethyl phenyl glycidate, Ethyl propionate, Ethyl safranate, Ethyl salicylate, Ethyl valerate, Eugenyl acetate, Evemyl, Fenchyl acetate, Floramat, Frescolat ML, Fructone, Fruitate, Geranyl acetate, Geranyl butyrate, Geranyl formate, Geranyl propionate, Geranyl tiglate, Givescone, Guaiol acetate, Hedionate, Hedione, Helvetolide, Herbanate, Hexyl acetate, Hexyl benzoate, n-Hexyl butyrate, Hexyl caproate, Hexyl isobutyrate, Hexyl propionate, Hexyl salicylate, Isobomyl acetate, Isobutyl acetate, Isobutyl phenyl acetate, Isobutyl salicylate, Isoeugenyl acetate, Isononyl acetate, Isopentyrate, Isopropyl 2-methyl butyrate, Isopropyl myristate, Jasmonyl, Liffarome, Linalyl acetate, Mahagonate, Manzanate, Menthanyl acetate, Menthyl acetate, Methyl benzoate, 2-Methyl butyl acetate, Methyl camomille, Methyl cinnamate, Methyl cyclogeranate, Methyl heptine carbonate, Methyl laurate, Methyl octine carbonate, Methyl phenyl acetate, Methyl salicylate, Methyl-2-methyl butyrate, Neofolione, Nopyl acetate, Octenyl acetate, Octyl acetate, Octyl isobutyrate, Para cresyl acetate, Para cresyl isobutyrate, Para cresyl phenyl acetate, Pear ester, Peranat, Phenoxy ethyl isobutyrate, Phenyl ethyl acetate, Phenyl ethyl butyrate, Phenyl ethyl formate, Phenyl ethyl isobutyrate, Phenyl ethyl phenyl acetate, Phenyl ethyl propionate, Phenyl ethyl salicylate, Phenyl ethyl tiglate, Phenyl propyl isobutyrate, Prenyl acetate, Romandolide, Sagecete, Styrallyl acetate, Styrallyl propionate, Tangerinol, Terpinyl acetate, Thesaron, Trans-2-hexenyl acetate, Tropicate, Verdox, Verdyl acetate, Verdyl propionate, Vertenex, Vetikol acetate, Vetiveryl acetate, Yasmolys.

Lactones such as: Ambrettolide, Arova N, Celeriax, Decalactone delta, Decalactone gamma, Dodecalactone delta, Dodecalactone gamma, Ethylene brassylate, Exaltolide, Heptalactone gamma, Hexalactone delta, Hexalactone gamma, Methyl laitone, Methyl octalactone, Nonalactone delta, Nonalactone gamma, Octahydrocoumarine, Octalactone delta, Octalactone gamma, Rootylone, Silvanone supra, Undecalactone delta, Undecalactone gamma, Valerolactone gamma, 10-Oxa HexaDecanolide (OHD musk), Coumarin, Habanolide, Jasmolactone.

Aldehydes such as: Acetaldehyde, Adoxal, Aldehyde C10, Aldehyde C11 iso, Aldehyde C11 moa, Aldehyde C11 undecylenic, Aldehyde C11 undecylic, Aldehyde C12 lauric, Aldehyde C12 MNA, Anisaldehyde, Amyl cinnamaldehyde, Benzaldehyde, Bourgeonal, Campholenaldehyde, Cantonal, Cetonal, Cinnamic aldehyde, Cis-4-decenal, Cis-6-nonenal, Citral, Citronellal, Citronellyl oxyacetaldehyde, Cocal, Cuminaldehyde, Curgix, Cyclal C, Cyclamen aldehyde, Cyclomyral, Cyclovertal, Decenal 9, Dupical, Empetal, Ethyl vanillin, Floralozone, Florhydral, Geraldehyde, Helional, Heliotropin, Heptanal, Hexanal, Hexyl cinnamaldehyde, Hivernal neo, Hydratropaldehyde, Hydroxycitronellal, Intreleven aldehyde, Isobutavan, Isocyclocitral, Isovaleraldehyde, Lilial, Limonenal, Maceal, Mefranal, Melonal, Methyl cinnamaldehyde, Nonadien-al trans-2 cis-6, Nonanal, Octanal, Oncidal, Para tolyl aldehyde, Phenyl acetaldehyde, Phenyl propyl aldehyde, Precyclemone B, Safranal, Salicylaldehyde, Scentenal, Syringa aldehyde, Trans-4-decenal, Trans-2-dodecenal, Trans-2-hexenal, Trans-2-nonenal, Trifernal, Vanillin, Veratraldehyde, Vernaldehyde Ketones such as: Acetanisol, Acetoin, Acetophenone, Aldron, Allyl ionone, Benzophenone, Benzyl acetone, Calone, Camphor, Carvone d-, Carvone l-, Cashmeran, Cedryl methyl ketone, Cepionate, Claritone, Cosmone, Crysolide, Cyclotene, Damascenone, Damascone alpha, Damascone beta, Damascone delta, Damascone gamma, Diacetyl, Dihydro beta ionone, Dihydro isojasmonate, Dimethyl octenone, Dynascone, Ethyl amyl ketone, Ethyl maltol, Fenchone, Filbertone, Geranyl acetone, Globanone, Heptyl cyclopentanone, Ionone alpha, Ionone beta, Ionone pure, Iriswood, Irone alpha, Iso E Super, Isofenchone, Isojasmone T, Isolone K, Isomenthone, Isophorone, Jasmone cis-, Kambernoir, Kephalis, Koavone, Lavendinal, Maltol, Menthone, Methyl acetophenone, Methyl amyl ketone, Methyl heptenone, Methyl hexyl ketone, Methyl ionone gamma, Methyl naphthyl ketone beta, Methyl nonyl ketone, Muscenone, Muscone, Nectaryl, Orinox, OTBC Ketone, Para tertbutylcyclohexanone, Patchwood, Phantolid, Pharaone, Piperitone, Plicatone, Raspberry ketone, Raspberry ketone methyl ether, Safraleine, Spirogalbanone pure, Tonalid, Trimofix O, Veloutone, Vetikon.

Alcohols such as: Alcohol oxo C13, Amber core, Ambermax, Ambrinol, Amyl vinyl carbinol, Anisic alcohol, Bacdanol, Benzyl alcohol, Butanol, Cedrol crystals, Cinnamic alcohol, Citronellol, Coranol, Decanol, Dimethyl benzyl carbinol, Dimethyl octanol, Dimethyl phenyl ethyl carbinol, Dimetol, Fenchol, Hexanol, Isoborneol, Isobornyl cyclohexanol, Javanol, Keflorol, Kohinool, Lauryl alcohol, Lilyflore, Linalool oxide, Mayol, Menthol, Norlimbanol, Octanol, Osyrol, Para tertbutylcyclohexanol, Phenoxanol, Phenoxyethanol, Phenyl ethyl alcohol, Phenyl propyl alcohol, Propylene glycol, Rosaphen, Rose glycol, St allyl alcohol, Tricyclodecane dimethanol, Tetrahydro linalool, Tetrahydro myrcenol, Timberol, Undecavertol, Cis-3-hexenol, Citronellol laevo, Cyclofloranol, Dihydrolinalool, Dihydromyrcenol, Dimyrcetol, Ebanol, Geraniol, Isopulegol, Linalool, Nerol, Nerolidol, Nonadien-ol trans-2 cis-6, Polysantol, Rosalva, Sandalmysore core, Sandalore, Terpinen-4-ol, Terpineol, Trans-2-hexenol Phenols such as: Butylated hydroxyanisole, Dihydroeugenol, Dimethyl hydroquinone, Dimethyl resorcinol, Eugenol pure, Guaiacol, Isoeugenol, Meta cresol, Methyl diantilis, Para cresol, Propenyl guaethol, Thymol, Ultravanil.

Ethers such as: Ambroxan, Anethole, Anther, Benzyl isoamyl ether, Benzyl isopropyl ether, Benzyl isovalerate, Boisiris, Cedramber, Cetalox, Decyl methyl ether, Dibenzyl ether, Dihydro rose oxide, Diphenyl oxide, Doremox, Estragole, Ethyl linalool, Eucalyptol, Galaxolide, Gyrane, Herbavert, Lime oxide, Madrox, Methyl isoeugenol, Naphthyl isobutyl ether beta, Nerol oxide, Nerolin bromelia, Para cresyl butyl ether, Para cresyl methyl ether, Petiole, Phenyl ethyl methyl ether, Rhubafuran, Rose oxide, Rosyrane, Trisamber, Vetylbois K, Yara yara Acetals such as: Acetal CD, Acetal R, Amberketal, Boisambrene forte, Citrathal, 1,1-Diethoxyethane, Emeraldine, Freshopal, Herboxane, Indoflor, Jacinthaflor, Magnolan, Spirambrene, Viridine, Elintaal, Glycolierral, Karanal, Methyl pamplemousse, Hydrocarbons such as: Bisabolene, Camphene, Carene delta 3, Caryophyllene, Cedrene, Cymene para, Dipentene, Diphenyl methane, Isolongifolene, Limonene d-, Longifolene, Myrcene, Naphthalene, Ocimene, Pinene alpha, Pinene beta, Styrene, Terpinene gamma, Terpinolene, 1,3,5-Undecatriene, Verdoracine.

Sulphur compounds such as: Corps cassis, Dibutyl sulphide, Dimethyl sulphide, Exovert, Grapefruit thiol, Oxane, Ribes mercaptan, Sulfurol, Thiocineol.

Nitriles such as: Cinnamyl nitrile, Citronellyl nitrile, Citronitrile, Clonal, Cumin nitrile, Hexyl cyclopentanone, Irisnitrile, Lemonile, Peonile, Tridecyl nitrile, Agrumen nitrile, n-decyl nitrile.

Oximes such as: Buccoxime, Labienoxime, Stemone.

Nitrogen heterocycles such as: 2-acetylpyrazine, 2-acetylpyridine, sec-butylquinoline, Corps racine, 2-ethyl-3,5(or 6)-dimethylpyrazine, Furfuryl pyrrole, Indole, Isobutyl quinoline, 2-Isobutyl-3(or 6)-methoxypyrazine, Isopropyl quinoline, Maritima, p-methyl quinoline, Skatol, 2,3,5-trimethylpyrazine.

Nitro compound such as: Musk Ketone

Schiff bases such as: Aurantiol, Helianthral, Ligantraal, Verdantiol.

Other materials such as: Acetanilide, Gardamide, Paradisamide, Dimethyl anthranilate, Methyl anthranilate, n-Butyric acid, Capric acid, Caproic acid, Caprylic acid, Phenylacetic acid, Caryophyllene oxide, Cedroxyde, Tobacarol The compounds of formula (5) or (6) can accordingly be used for the production of compositions and, as will be evident from the foregoing compilation, a wide range of known odorants/fragrance, flavor and/or deodorizing/masking materials. In the production of such compositions, the known fragrance, flavor and/or deodorizing/masking materials referred to earlier can be used according to methods which are known to the perfumer such as, for example, according to W. A. Poucher, Perfumes, Cosmetics and Soaps 2, 7th Edition, Chapman and Hall, London 1974.

In an embodiment of the present invention, the claimed fragrance, flavor and/or deodorizing/masking composition comprises in addition to the ketones at least one ester and/or one alcohol, preferably at least a mixture of ester and alcohol; the said ester and/or alcohol are preferably selected from the list defined herein above. In an embodiment of the present invention, the claimed odorant composition is characterised by a total content of the compound(s) of formula (5) or of formula (6) together with the ester(s) and/or alcohol(s) which is superior to 25 wt %, preferably superior to 50 wt %, for example superior to 75 wt %, or even superior to 90 wt %.

The disclosure is further illustrated by the following examples which in no way should be construed as being further limiting. One skilled in the art will readily appreciate that the specific methods and results described are merely illustrative.

All stereoisomers of the compounds of the instant disclosure are contemplated, either in admixture or in pure or substantially pure form. The compounds of the present disclosure can have asymmetric centers at any of the carbon atoms, consequently, claimed compounds can exist in enantiomeric, or diastereomeric forms, or in mixtures thereof. The processes for preparation can utilize racemates, (pure) enantiomers, nonracemic mixtures of enantiomers, diastereomers or mixtures of diastereomers as starting materials. When diastereomeric or enantiomeric products are obtained as mixtures, they can be separated by conventional methods for example, chromatographic separation or fractional crystallization or through diastereomeric salt formation. When intended, a desired enantiomer or diastereomer can also be obtained by following appropriate enantioselective or diastereoselective reactions.

SYNTHESIS EXAMPLES

Example 1

Synthesis of 3,3,4-tri ethylpent-4-en-2-one

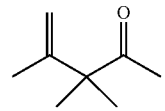

2,3-Dimethyl-2-butene (510 g, 5.94 mol, 1 equiv) was added to a solution of zinc chloride (243 g, 1.78 mol, 0.3 equiv) in acetic anhydride (1.04 kg, 10.2 mol, 1.71 equiv) at 5° C. under nitrogen atmosphere while stirring. The mixture was stirred in an ice bath and left to reach 20° C. within 24 h. Subsequently, water (1.50 L) was added and the mixture was extracted with methyl tert-butyl ether (3×500 mL). The combined organic phases were washed successively with water (2×750 mL), aqueous saturated $Na_2CO_3$ (to pH 7) and brine (750 mL). The organic phase was dried over $Na_2SO_4$ and volatiles were removed under reduced pressure. The residue (960 g) was distilled in vacuo (57° C./55 mbar) to afford 3,3,4-trimethylpent-4-en-2-one (501 g, 66%).

$^1$H NMR (400 MHz, $CDCl_3$): δ 1.15 (s, 6H), 1.58 (s, 3H), 1.98 (s, 3H), 4.89 (s, 2H).

$^{13}$C NMR (100 MHz, $CDCl_3$): δ 19.2, 22.2, 23.9, 53.0, 110.6, 146.8, 210.9.

Example 2

Synthesis of 4,4,5-trimethylhex-5-en-3-one

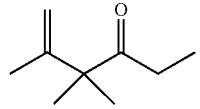

2,3-Dimethyl-2-butene (1.17 kg, 14.0 mol, 1 equiv) was added to a solution of zinc chloride (565 g, 4.15 mol, 0.3 equiv) in propionic anhydride (2.50 kg, 19.2 mol, 1.38 equiv) at 5° C. under nitrogen atmosphere while stirring. The mixture was stirred in an ice bath and left to reach 20° C. within 24 h. The mixture was washed with water (3×3.00 L), mixture of ice-cold water (1 L) and aqueous saturated sodium carbonate (1.75 L), water (1×500 mL), and brine (1×500 mL). Organic fraction was separated and was distilled in vacuo (69° C./35 mbar) to afford 4,4,5-trimethylhex-5-en-3-one (1.01 kg, 51%).

$^1$H NMR (400 MHz, $CDCl_3$): δ 0.92 (t, J=7.2 Hz, 3H), 1.15 (s, 6H), 1.56 (s, 3H), 2.35 (q, J=7.2 Hz, 2H), 4.87 (s, 2H). $^{13}$C NMR (100 MHz, $CDCl_3$): δ 8.3, 20.1, 23.3, 29.5, 53.5, 111.4, 148.0, 214.4.

Example 3

Synthesis of 2,3,3-trimethylhept-1-en-4-one

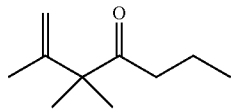

2,3-Dimethyl-2-butene (930 g, 11.0 mol, 1 equiv) was added to a solution of zinc chloride (452 g, 3.31 mol, 0.3 equiv) in butyric anhydride (1.75 kg, 11.0 mol, 1 equiv) at 5° C. under nitrogen atmosphere while stirring. The mixture was warmed to 20° C. within 6 h and then stirred at 20° C. for 48 h. The reaction mixture was washed successively with water (2×4.0 L), aqueous saturated $Na_2CO_3$ (to pH 7) and brine (1.0 L). The organic fraction was separated (1.55 kg) and was distilled in vacuo (59° C./10 mbar) to afford 2,3,3-trimethylhept-1-en-4-one (1.24 kg, 60%).

$^1$H NMR (400 MHz, $CDCl_3$): δ 0.80 (t, J=7.6 Hz, 3H), 1.15 (s, 6H), 1.43-1.52 (m, 2H), 1.55 (s, 3H), 2.31 (t, J=7.2 Hz, 2H), 4.88 (s, 2H).

Example 4

Synthesis of 2,3,3-trimethyloct-1-en-4-one: Prepared as in example 1; yield 91.0 g (37%)

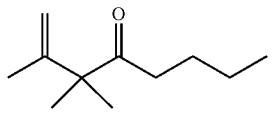

$^1$H NMR (400 MHz, $CDCl_3$): δ 0.81 (t, J=7.2 Hz, 3H), 1.15-1.24 (m, 8H), 1.39-1.46 (m, 2H), 1.57 (s, 3H), 2.32 (t, J=7.6 Hz, 2H), 4.88 (s, 2H).
$^{13}$C NMR (100 MHz, $CDCl_3$): δ 14.0, 20.3, 22.5, 23.4, 26.4, 36.2, 53.8, 111.7, 148.1, 214.0.

Example 5

Synthesis of 2,3,3,6-tetramethylhept-1-en-4-one: Prepared as in example 1; yield 34%

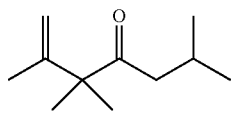

Example 6

Synthesis of 2,3,3-trimethylnon-1-en-4-one: Prepared as in example 1; yield 69.2 g (38%)

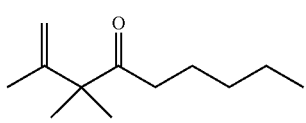

$^1$H NMR (400 MHz, $CDCl_3$) 0.80 (t, J=7.2 Hz, 3H), 1.15-1.25 (m, 10H), 1.40-1.48 (m, 2H), 1.56 (s, 3H), 2.32 (t, J=7.6 Hz, 2H), 4.87 (s, 2H); $^{13}$C NMR (100 MHz, $CDCl_3$): δ 14.0, 20.3, 22.6, 23.4, 23.9, 31.6, 36.4, 53.8, 111.7, 148.1, 214.0.

Example 7

Synthesis of 2,4,4,5-tetramethylhex-5-en-3-one

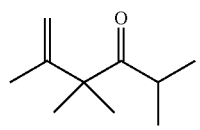

To a solution of 4,4,5-trimethylhex-5-en-3-one (45.0 g, 321 mmol) in tetrahydrofuran (1.80 L) potassium 2-methylpropan-2-olate (54.0 g, 481 mmol) was added at 0° C., over a period of 40 min under nitrogen atmosphere. The mixture was stirred between 0-5° C. for 30 min. Then iodomethane (49.9 mL, 802 mmol) was added dropwise and the mixture was allowed to warm to 20° C. and then stirred for 16 h. Subsequently, saturated aqueous $NH_4Cl$ solution was added (200 mL) and the mixture extracted with ethyl acetate (2×200 mL). Combined organic fraction was dried over anhydrous $Na_2SO_4$ and volatiles were removed under reduced pressure. Crude product (65.6 g) was purified by fractional distillation using ss-packed column (39° C./3 mbar) to afford 2,4,4,5-tetramethylhex-5-en-3-one (36.2 g, 65.8%) as colorless liquid.

$^1$H NMR (600 MHz, $CDCl_3$): δ 1.00 (d, J=6.7 Hz, 6H), 1.25 (s, 6H), 1.66 (s, 3H), 3.03-3.11 (m, 1H), 5.00 (br. d, J=7.1 Hz, 1H).
$^{13}$C NMR (151 MHz, $CDCl_3$): δ 20.6, 20.8, 23.1, 34.0, 54.4, 112.3, 147.3, 218.2.

Example 8

Synthesis of 3,3,4-trimethylpentan-2-one

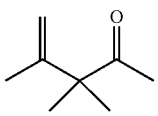

Raney Ni (20.0 mg, 340 μmol) was added to a solution of 3,3,4-trimethylpent-4-en-2-one (2.50 g, 19.5 mmol) in isopropanol (12 mL) at 25° C. and the reaction mixture was stirred under hydrogen atmosphere at 60° C./14 bar for 48 h. The reaction mixture was cooled to 25° C., filtered through a pad of celite and the solvent was removed under reduced pressure to afford 3,3,4-trimethylpentan-2-one (2.40 g, 94%).

Example 9

Synthesis of 2,3,3,6-trimethylhepta-1,5-dien-4-one

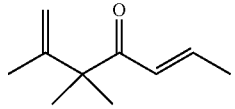

2,3-Dimethyl-1-butene (284 g, 405 mL, 3.38 mol) was added to a solution of trifluoromethanesulfonic acid (5.07 g, 3.0 mL, 33.8 mmol) in crotonic anhydride (521 g, 500 mL, 3.38 mol) at −20° C. under nitrogen atmosphere. Then the mixture was stirred at 0° C. for 30 min, and at 20° C. for 12 h. Subsequently, 2M sodium hydroxide solution (2.53 L, 5.07 mol) was added, the mixture was stirred at 50° C. for 4 hours under nitrogen atmosphere and cooled to 20° C. Then organic fraction was separated and the aqueous fraction was washed with methyl tertbutyl ether. The combined organic fractions were washed with brine, and dried over $Na_2SO_4$ The volatiles were removed under reduced pressure and the residue distilled in vacuo (50-52° C./4 mbar) to afford 2,3,3,6-trimethylhepta-1,5-dien-4-one (142 g, 22% yield).

$^1$H NMR (600 MHz, CDCl$_3$) δ 6.95 (dq, J=13.9, 6.9 Hz, 1H), 6.45-6.31 (m, 1H), 4.98 (d, J=3.6 Hz, 2H), 1.85 (dd, J=6.9, 1.6 Hz, 3H), 1.64 (s, 3H), 1.23 (s, 6H).

$^{13}$C NMR (151 MHz, CDCl$_3$) δ 202.01, 148.05, 142.58, 126.23, 111.76, 52.36, 23.16, 20.26, 18.15.

Example 10

Synthesis of 2,3,3,6-tetramethylhepta-1,5-dien-4-one

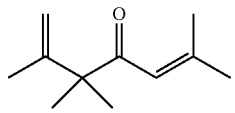

A mixture of titanium tetrachloride (15.8 g, 83.0 mmol) and tributylamine (17.1 g, 92.0 mmol) was added to a solution of 3,3,4-trimethylpent-4-en-2-one (10.0 g, 79.0 mmol) in dichloromethane (100 mL) at −60° C. under nitrogen atmosphere. Then the mixture was warmed to 20° C. and stirred for 30 min. Subsequently, acetone (4.70 g, 81.0 mmol) was added in one portion and the mixture was stirred for 1 h. Then the reaction mixture was cooled to −55° C. and pyridine (31.3 g, 396 mmol) was added and the mixture was left to reach 20° C.

The pale brown suspension was filtered over decalite and paper and the filtrate was purified by flash chromatography on silicagel with cyclohexane/methyl tertbutyl ether mixture as eluent. The product was distilled in vacuo applying kugelrohr apparatus (110° C./7 mbar) to afford 2,3,3,6-tetramethylhepta-1,5-dien-4-one (3.50 g, 26%) as colorless oil.

$^1$H NMR (500 MHz, CDCl$_3$) δ 6.24-6.15 (m, 1H), 4.94 (dd, J=7.8, 6.5 Hz, 2H), 2.13 (d, J=1.0 Hz, 3H), 1.87 (d, J=1.0 Hz, 3H), 1.65 (s, 3H), 1.22 (s, 6H).

$^{13}$C NMR (126 MHz, CDCl$_3$) δ 203.65, 155.75, 149.01, 148.86, 120.04, 111.02, 53.19, 27.82, 23.45, 20.72, 20.25.

Example 11

Synthesis of (E)-2,3,3-trimethyl-6-phenylhepta-1,5-dien-4-one

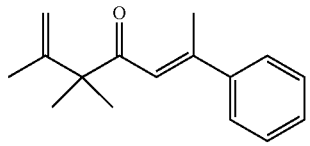 [SMILES: C=C(C)C(C)(C)C(=O)/C=C(\C)c1ccccc1]

A mixture of titanium tetrachloride (15.8 g, 83.0 mmol) and tributylamine (17.1 g, 92.0 mmol) was added to a solution of 3,3,4-trimethylpent-4-en-2-one (10.0 g, 79.0 mmol) in dichloromethane (100 mL) at −60° C. under nitrogen atmosphere. Then the mixture was warmed to 20° C. and stirred for 30 min. Subsequently, acetophenone (9.50 g, 79.0 mmol) added in one portion and the mixture was stirred for 1 h. Then the reaction mixture was cooled to −55° C. and pyridine (31.3 g, 396 mmol) was added and the mixture was left to reach 20° C. The crude material was filtered over paper, and the filtrate was purified by flash chromatography on silicagel with cyclohexane/methyl tert-butyl ether mixture as eluent. The product was distilled in vacuo applying kugelrohr apparatus (150° C./6 mbar) to afford (E)-2,3,3-trimethyl-6-phenylhepta-1,5-dien-4-one (4.17 g, 21%)

$^1$H NMR (500 MHz, CDCl$_3$) δ 7.43 (dd, J=7.9, 1.8 Hz, 2H), 7.36 (dd, J=7.0, 0.8 Hz, 3H), 6.66 (d, J=1.3 Hz, 1H), 4.99 (dd, J=10.8, 9.5 Hz, 2H), 2.53 (d, J=1.3 Hz, 3H), 1.70 (s, 3H), 1.29 (s, 6H).

$^{13}$C NMR (126 MHz, CDCl$_3$) δ 204.13, 154.32, 148.74, 143.06, 128.90, 128.51, 126.52, 121.06, 111.44, 53.81, 23.53, 20.34, 18.42.

The olfactory properties of the compounds of formula (5-6) selected from above are given in the below table

| Compounds of formula (5)-(6) | IUPAC name | Olfactory notes |
|---|---|---|
|  | 3,3,4-Trimethyl-pent-4-en-2-one | Camphoraceous, *eucalyptus*, piny |

| Compounds of formula (5)-(6) | IUPAC name | Olfactory notes |
|---|---|---|
| | 4,4,5-Trimethyl-hex-5-en-3-one | Camphoraceous, piny |
| | 2,4,4,5-tetramethylhex-5-en-3-one | Camphoraceous, slightly fruity, earthy |
| | 2,3,3-Trimethyl-octa-1,7-dien-4-one | *Thuja*, coniferous, balsamic, dried fruity |
| | 2,4,4,5-tetramethylhexan-3-one | Earthy, camporaceous, minty, slightly floral-fruity |
| | 2,3,3-trimethylheptan-4-one | Floral, camphoraceous |
| | 2,3,3-Trimethyl-hepta-1,5-dien-4-one | Strong, diffusive, fruity, prune, armoise, *artemisia*, dried fruits, sultains, metallic |
| | 2,3,3,6-tetramethylhepta-1,5-dien-4-one | Dried fruits, plum, floral, camphoraceous, herbaceous, slightly earthy, woody, cooling effect |

Compositions Examples

In the following invention example (12) and comparative example (13), commercial compounds and/or a product of example 9 were included in a rose accord fragrance. DPG=dipropylene glycol, Keflorol=2-isobutyl-4-methyltetrahydro-2H-pyran-4-ol.

Example 12 and Comparative Example 13—Rose Accord

| Raw material | Ex. 12 Parts | Ex. 13 Parts |
|---|---|---|
| Phenylethanol | 400 | 400 |
| Geraniol 80 | 200 | 200 |
| Citronellol 96 | 90 | 90 |
| Geranyl acetate | 75 | 75 |
| Keflorol 90 | 75 | 75 |
| PTBCHA | 35 | 35 |
| Eugenol | 20 | 20 |
| Rose oxide | 5 | 5 |
| 2,3,3-Trimethyl-hepta-1,5-dien-4-one | 0.1 | 0 |
| DPG | 99.9 | 100 |
| Total | 1000 | 1000 |

The introduction of 0.01% by weight of 2,3,3-trimethyl-hepta-1,5-dien-4-one (product from example 9) provides this rosy accord with a natural Turkish rose oil impression, juiciness and fruity top note and enhances floral and geranium notes while rendering metallic note of rose oxide and spicy note of eugenol, making the composition more round, rich and smooth at the same time.

The invention claimed is:
1. A fragrance, flavor and/or deodorizing/masking compositions having coniferous, thuya, floral, and/or fruity olfactory notes comprising a ketone selected from compounds of formula (5) or of formula (6);

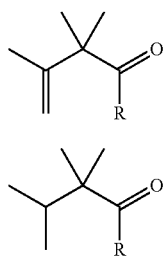

Formula (5)

Formula (6)

wherein R is an alkyl group having from 1 to 9 carbon atoms, an alkenyl group containing only one carbon-carbon double bond and having up to 9 carbon atoms, an (substituted) aryl group having up to 9 carbon atoms, an oxo-alkyl group having up to 9 carbon atoms, an alkoxyaryl group containing up to 9 carbon atoms or a (substituted) benzyl group having up to 9 carbon atoms.

2. The fragrance, flavor and/or deodorizing/masking compositions according to claim 1 wherein R is methyl, ethyl, n-propyl, i-propyl, n-butyl, s-butyl, t-butyl, i-butyl, 2-pentyl, 3-pentyl, cyclopropyl, cyclobutyl, cyclopentyl, cyclohexyl, 1-(cyclohexylmethyl), (methoxy)methyl, (ethoxy)methyl, 1-propenyl, 1-isobutenyl, 3-butenyl, 5-(2-methylpent-2-en)yl, 4-penten-2-enyl, 4-pent-1-enyl, 4-(4-methylpent-1-en)yl, 5-(2,5-dimethylhex-2-en)yl, benzyl, phenyl, or 4-methoxyphenyl.

3. The fragrance, flavor and/or deodorizing/masking compositions according to claim 1 wherein the ketone is selected from:

| Structure | Chemical name |
|---|---|
| 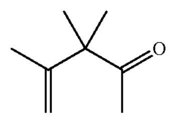 | 3,3,4-trimethylpent-4-en-2-one |
| 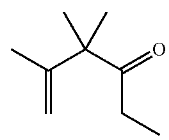 | 4,4,5-trimethylhex-5-en-3-one |
| 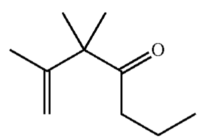 | 2,3,3-trimethylhept-1-en-4-one |
| 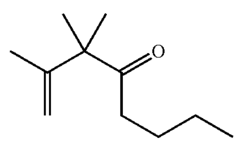 | 2,3,3-trimethyloct-1-en-4-one |
| 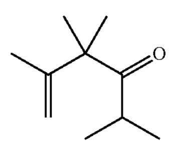 | 2,4,4,5-tetramethylhex-5-en-3-one |
| 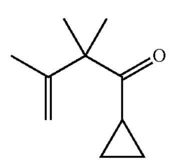 | 1-cyclopropyl-2,2,3-trimethylbut-3-en-1-one |
| 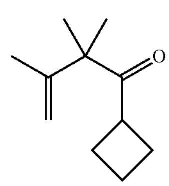 | 1-cyclobutyl-2,2,3-trimethylbut-3-en-1-one |
| 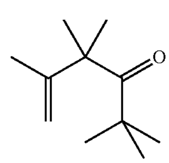 | 2,2,4,4,5-pentamethylhex-5-en-3-one |

| Structure | Chemical name |
|---|---|
| 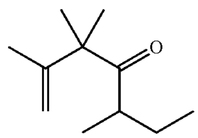 | 2,3,3,5-tetramethylhept-1-en-4-one |
| 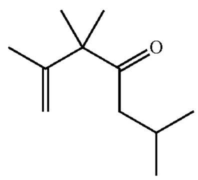 | 2,3,3,6-tetramethylhept-1-en-4-one |
| 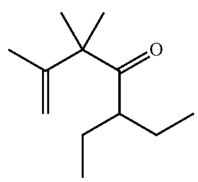 | 5-ethyl-2,3,3-trimethylhept-1-en-4-one |
| 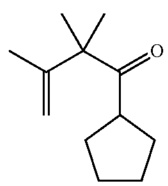 | 1-cyclopentyl-2,2,3-trimethylbut-3-en-1-one |
| 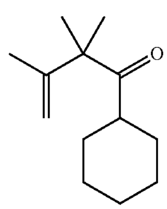 | 1-cyclohexyl-2,2,3-trimethylbut-3-en-1-one |
| 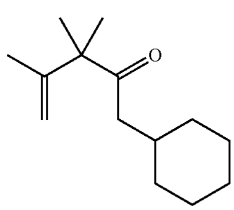 | 1-cyclohexyl-3,3,4-trimethylpent-4-en-2-one |
| 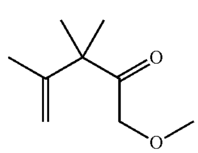 | 1-methoxy-3,3,4-trimethylpent-4-en-2-one |
| 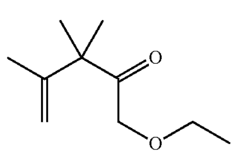 | 1-ethoxy-3,3,4-trimethylpent-4-en-2-one |

-continued

| Structure | Chemical name |
|---|---|
| 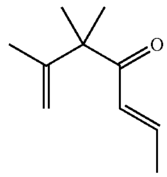 | 2,3,3-trimethylhepta-1,5-dien-4-one |
| 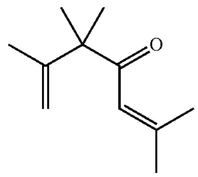 | 2,3,3,6-tetramethylhepta-1,5-dien-4-one |
| 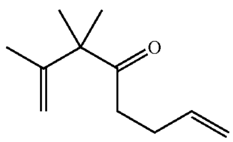 | 2,3,3-trimethylocta-1,7-dien-4-one |
| 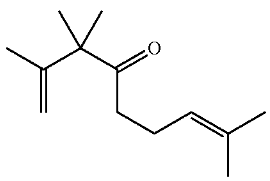 | 2,3,3,8-tetramethylnona-1,7-dien-4-one |
| 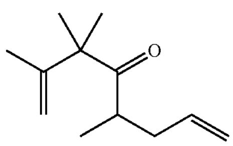 | 2,3,3,5-tetramethylocta-1,7-dien-4-one |
| 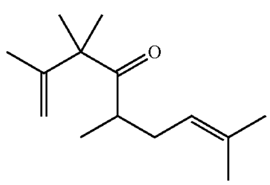 | 2,3,3,5,8-pentamethylnona-1,7-dien-4-one |
| 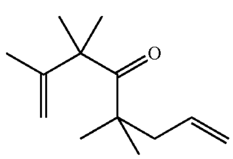 | 2,3,3,5,5-pentamethylocta-1,7-dien-4-one |
| 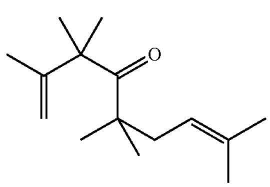 [SMILES: C=C(C)C(C)(C)C(=O)C(C)(C)CC=C(C)C] | 2,3,3,5,5,8-hexamethylnona-1,7-dien-4-one |
| 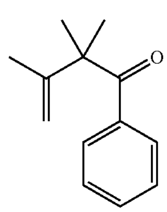 | 2,2,3-trimethyl-1-phenylbut-3-en-1-one |

| Structure | Chemical name |
|---|---|
| 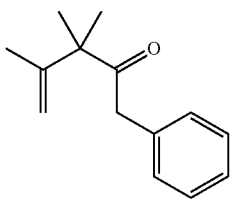 | 3,3,4-trimethyl-1-phenylpent-4-en-2-one |
| 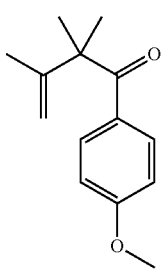 [SMILES: C=C(C)C(C)(C)C(=O)c1ccc(OC)cc1] | 1-(4-methoxyphenyl)-2,2,3-trimethylbut-3-en-1-one |
| 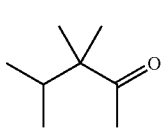 | 3,3,4-trimethylpentan-2-one |
| 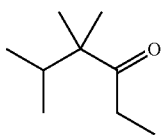 | 4,4,5-trimethylhexan-3-one |
| 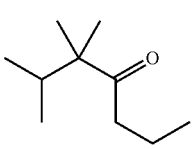 | 2,3,3-trimethylheptan-4-one |
| 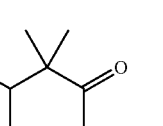 | 2,3,3-trimethyloctan-4-one |
| 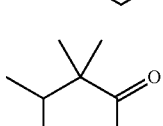 | 2,4,4,5-tetrmethylhexan-3-one |
| 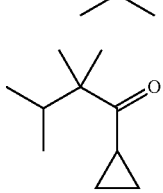 | 1-cyclopropyl-2,2,3-trimethylbutan-1-one |
| 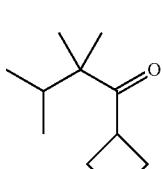 | 1-cyclobutyl-2,2,3-trimethylbutan-1-one |

-continued

| Structure | Chemical name |
|---|---|
| 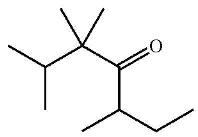 | 2,3,3,5-tetramethylheptan-4-one |
| 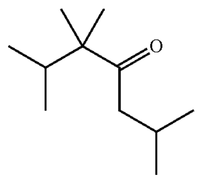 | 2,3,3,6-tetramethylheptan-4-one |
| 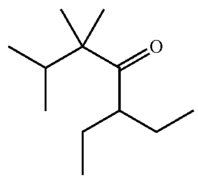 | 5-ethyl-2,3,3-trimethylheptan-4-one |
| 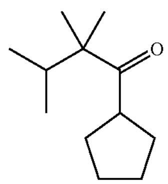 | 1-cyclopentyl-2,2,3-trimethylbutan-1-one |
| 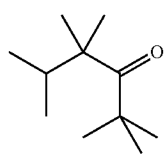 | 2,2,4,4,5-pentamethylhexan-3-one |
| 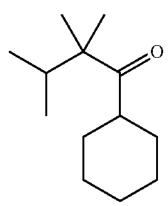 | 1-cyclohexyl-2,2,3-trimethylbutan-1-one |
| 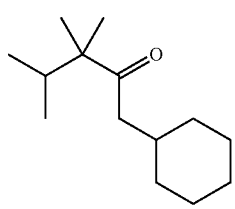 | 1-cyclohexyl-3,3,4-trimethylpentan-2-one |
| 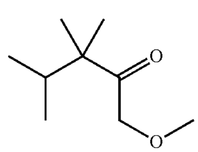 | 1-methoxy-3,3,4-trimethylpentan-2-one |
| 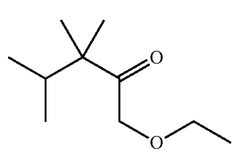 | 1-ethoxy-3,3,4-trimethylpentan-2-one |

-continued

| Structure | Chemical name |
|---|---|
| 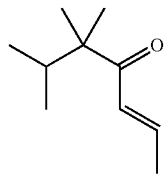 | 5,5,6-trimethylhept-2-en-4-one |
| 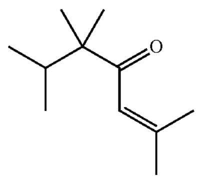 | 2,5,5,6-tetramethylhept-2-en-4-one |
| 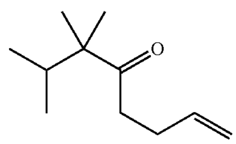 | 2,3,3-trimethyloct-7-en-4-one |
| 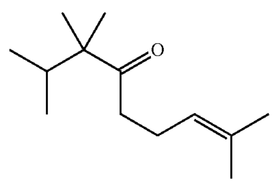 | 2,3,3,8-tetramethylnon-7-en-4-one |
| 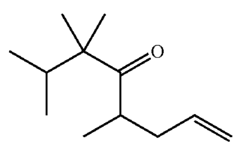 | 2,3,3,5-tetramethyloct-7-en-4-one |
| 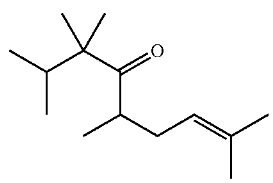 | 2,3,3,5,8-pentamethylnon-7-en-4-one |
| 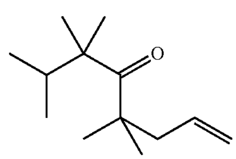 | 2,3,3,5,5-pentamethyloct-7-en-4-one |
| 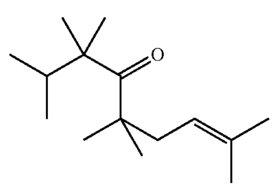 | 2,3,3,5,5,8-hexamethylnon-7-en-4-one |
| 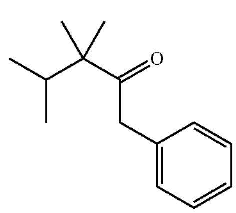 | 3,3,4-trimethyl-1-phenylpentan-2-one |

-continued

| Structure | Chemical name |
|---|---|
| 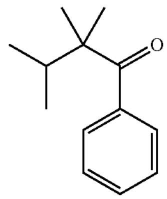 | 2,2,3-trimethyl-1-phenylbutan-2-one |
| | 1-(4-methoxyphenyl)-2,2,3-trimethylbutan-1-one | and/or a mixture of two or more of the said compounds.

4. The fragrance, flavor and/or deodorizing/masking compositions according to claim 1, wherein the content of the compounds of formula (5) and/or of formula (6) is comprised between 0.00001 and 99.9 wt. %.

5. The fragrance, flavor and/or deodorizing/masking compositions according to claim 1, additionally comprising at least one ester and/or one alcohol.

6. The fragrance, flavor and/or deodorizing/masking compositions according to claim 5, wherein the total content of the compound(s) of formula (5) and/or of formula (6) together with the ester(s) and/or alcohol(s) is superior to 25 wt %.

7. The fragrance, flavor and/or deodorizing/masking compositions according to claim 1, comprising a mixture of ketone compounds according to formula (5) and/or formula (6) wherein the weight ratio between the ketone present in highest weight and the ketone present in the second highest weight in the mixture is comprised between 99.9% and 50%.

8. The fragrance, flavor and/or deodorizing/masking compositions according to claim 7, wherein the difference of the number of carbon atoms between one ketone and another ketone in the mixture is between 1 and 3, or between 1 and 2.

9. The fragrance, flavor and/or deodorizing/masking, compositions according to claim 7, wherein one ketone belongs to formula (5), one ketone belongs to formula (6), and said two ketones have the same number of carbon atoms.

10. A ketone useful in a fragrance, flavor and/or deodorizing/masking composition according to claim 1 wherein the ketone is selected from:

| Structure | Chemical name |
|---|---|
| 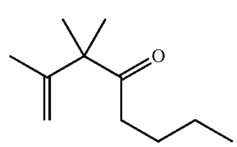 | 2,3,3-trimethyloct-1-en-4-one |
| 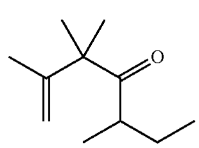 | 2,3,3,5-tetramethylhept-1-en-4-one |
| 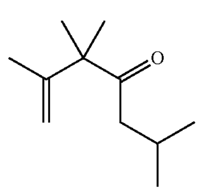 | 2,3,3,6-tetramethylhept-1-en-4-one |

-continued

| Structure | Chemical name |
|---|---|
| 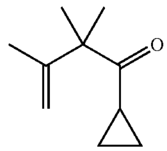 | 1-cyclopropyl-2,2,3-trimethylbut-3-en-1-one |
| 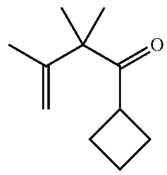 | 1-cyclobutyl-2,2,3-trimethylbut-3-en-1-one |
| 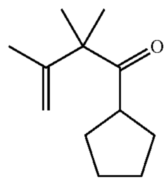 | 1-cyclopentyl-2,2,3-trimethylbut-3-en-1-one |
| 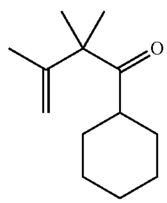 | 1-cyclohexyl-2,2,3-trimethylbut-3-en-1-one |
| 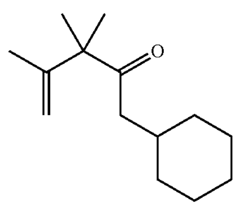 | 1-cyclohexyl-3,3,4-trimethylpent-4-en-2-one |
| 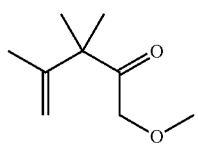 | 1-methoxy-3,3,4-trimethylpent-4-en-2-one |
| 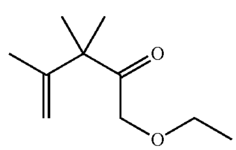 | 1-ethoxy-3,3,4-trimethylpent-4-en-2-one |
| 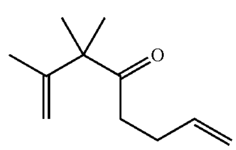 | 2,3,3-trimethylocta-1,7-dien-4-one |
| 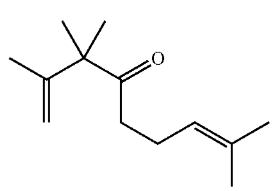 | 2,3,3,8-tetramethylnona-1,7-dien-4-one |

-continued

| Structure | Chemical name |
|---|---|
| 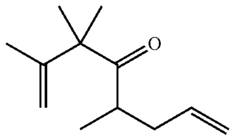 | 2,3,3,5-tetramethylocta-1,7-dien-4-one |
| 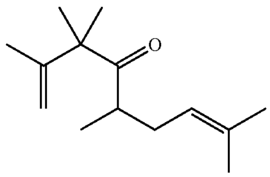 | 2,3,3,5,8-pentamethylnona-1,7-dien-4-one |
| 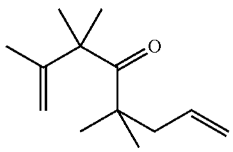 | 2,3,3,5,5-pentamethylocta-1,7-dien-4-one |
| 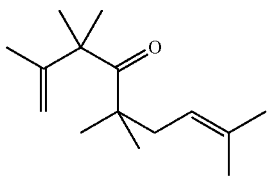 | 2,3,3,5,5,8-hexamethylnona-1,7-dien-4-one |
| 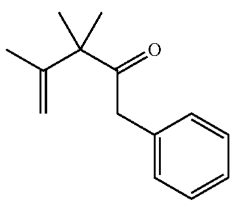 | 3,3,4-trimethyl-1-phenylpent-4-en-2-one |
| 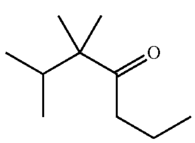 | 2,3,3-trimethylheptan-4-one |
| 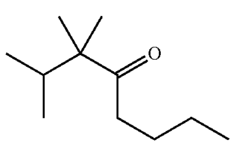 | 2,3,3-trimethyloctan-4-one |
| 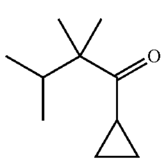 | 1-cyclopropyl-2,2,3-trimethylbutan-1-one |
| 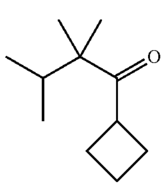 | 1-cyclobutyl-2,2,3-trimethylbutan-1-one |

-continued

| Structure | Chemical name |
|---|---|
| 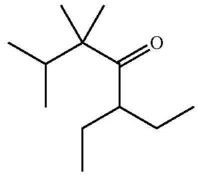 | 5-ethyl-2,3,3-trimethylheptan-4-one |
| 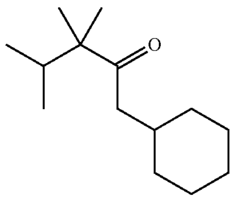 | 1-cyclohexyl-3,3,4-trimethylpentan-2-one |
| 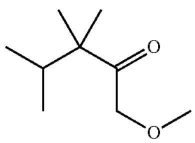 | 1-methoxy-3,3,4-trimethylpentan-2-one |
| 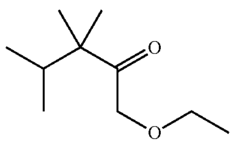 | 1-ethoxy-3,3,4-trimethylpentan-2-one |
| 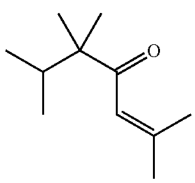 | 2,5,5,6-tetramethylhept-2-en-4-one |
| 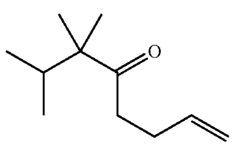 | 2,3,3-trimethyloct-7-en-4-one |
| 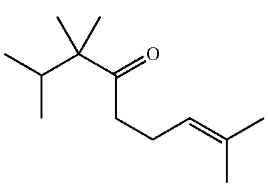 | 2,3,3,8-tetramethylnon-7-en-4-one |
| 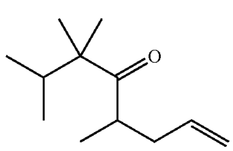 | 2,3,3,5-tetramethyloct-7-en-4-one |
| 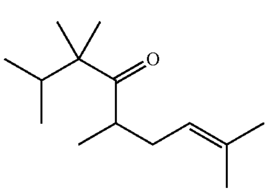 | 2,3,3,5,8-pentamethylnon-7-en-4-one |

| Structure | Chemical name |
|---|---|
| 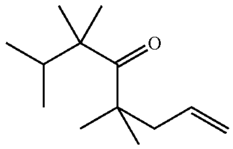 | 2,3,3,5,5-pentamethyloct-7-en-4-one |
| 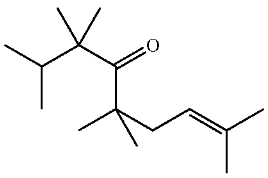 [SMILES: CC(C)=CCC(C)(C)C(=O)C(C)(C)C(C)C] | 2,3,3,5,5,8-hexamethylnon-7-en-4-one |
| 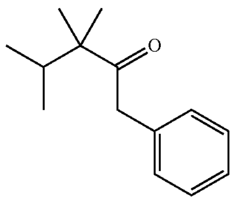 | 3,3,4-trimethyl-1-phenylpentan-2-one |
| 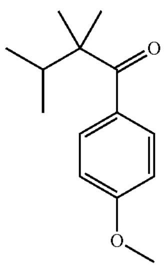 [SMILES: COc1ccc(C(=O)C(C)(C)C(C)C)cc1] | 1-(4-methoxyphenyl)-2,2,3-trimethylbutan-1-one. |

11. A mixture of ketone compounds according to claim 10, wherein the weight ratio between the ketone present in highest weight and the ketone present in the second highest weight in the mixture is comprised between 99.9% and 50%.

12. A mixture of ketone compounds according to claim 11, wherein the difference of the number of carbon atoms between one ketone and another ketone in the mixture is between 1 and 9.

13. A mixture of ketone compounds according to claim 11, wherein one ketone belongs to formula (5) as defined in claim 1, one ketone belongs to formula (6) as defined in claim 1, and said two ketones have the same number of carbon atoms.

14. A fragrance, flavor and/or deodorizing/masking compositions according to claim 1, wherein the ketone(s) is(are) prepared by subjecting 2,3-dimethylbutene(s) to an acylation reaction step, said compositions also comprising, in addition to the ketone(s), at least one of the side product(s) obtained during the said acylation reaction step.

15. A fragrance, flavor and/or deodorizing/masking composition according to claim 1 in a perfumed or flavored product.

16. A ketone according to claim 10 in a perfumed or flavored product.

17. The Fragrance, flavor and/or deodorizing/masking compositions according to claim 7 wherein the difference of the number of carbon atoms between one ketone and another ketone in the mixture is between 1 and 2.

18. A process for the preparation of ketones selected from compounds of formula (5) or of formula (6)

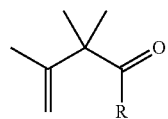

Formula (5)

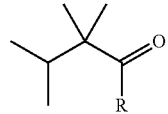

Formula (6)

wherein R is an alkyl group having from 1 to 9 carbon atoms, an alkenyl group containing only one carbon-carbon double bond and having up to 9 carbon atoms, an (substituted) aryl group having up to 9 carbon atoms, an oxo-alkyl group having up to 9 carbon atoms, an alkoxyaryl group containing up to 9 carbon atoms or a (substituted) benzyl group having up to 9 carbon atoms, wherein the compounds of Formula (5) are prepared by subjecting 2,3-dimethylbutene(s) to an acylation reaction step in the presence of a Brønsted acid catalyst, optionally followed by either an alkylation or an aldol condensation step, to form the compounds of Formula (5), and/or wherein the compounds of Formula (6) are prepared by subjecting 2,3-dimethylbutene(s) to an acylation reaction step in the presence of a Brønsted acid catalyst, optionally followed by either an alkylation or an aldol condensation step, to form the compounds of Formula (5) and by subjecting the said compounds of Formula (5) to a hydrogenation reaction step to form the compounds of Formula (6).

19. The process for the preparation of ketones according to claim 18, wherein the Brønsted acid catalyst is methylsulfonic acid or trifluoromethylsulfonic acid.

20. The process for the preparation of ketones according to claim 18, wherein the 2,3-dimethylbutenes compounds are a mixture of 2,3-dimethyl-2-butene and 2,3-dimethyl-1-butene.

* * * * *